US011762108B2

(12) United States Patent
Harmon

(10) Patent No.: US 11,762,108 B2
(45) Date of Patent: Sep. 19, 2023

(54) MODULAR PET DETECTOR COMPRISING A PLURALITY OF MODULAR ONE-DIMENSIONAL ARRAYS OF MONOLITHIC DETECTOR SUB-MODULES

(71) Applicant: LightSpin Technologies Inc., Endicott, NY (US)

(72) Inventor: Eric Harmon, Norfolk, MA (US)

(73) Assignee: LightSpin Technologies Inc., Endicott, NY (US)

( * ) Notice: Subject to any disclaimer, the term of this patent is extended or adjusted under 35 U.S.C. 154(b) by 59 days.

(21) Appl. No.: 17/154,217

(22) Filed: Jan. 21, 2021

(65) Prior Publication Data

US 2021/0223414 A1 Jul. 22, 2021

Related U.S. Application Data

(60) Provisional application No. 62/963,656, filed on Jan. 21, 2020, provisional application No. 63/055,027, filed on Jul. 22, 2020.

(51) Int. Cl.
*A61B 6/03* (2006.01)
*G01T 1/20* (2006.01)
(Continued)

(52) U.S. Cl.
CPC .......... *G01T 1/20182* (2020.05); *A61B 6/037* (2013.01); *A61B 6/4233* (2013.01);
(Continued)

(58) Field of Classification Search
CPC ......... A61B 6/037; A61B 6/42; A61B 6/4208; A61B 6/4233; A61B 6/4241;
(Continued)

(56) References Cited

U.S. PATENT DOCUMENTS 5,487,098 A * 1/1996 Dobbs ................... A61B 6/032
378/19
5,635,718 A * 6/1997 DePuydt ........... H01L 27/14636
250/208.1
(Continued)

OTHER PUBLICATIONS

M. Bieniosek, "Electronic Readout Strategies for Silicon Photomultipler-Based Positron Emisson Tomography Detectors", Mar. 2016, p. 1-121, Stanford University.
(Continued)

*Primary Examiner* — Allen C. Ho
(74) *Attorney, Agent, or Firm* — Intrinsic Law Corp.

(57) ABSTRACT

A gamma-ray detector includes a plurality of modular one-dimensional arrays of monolithic detector sub-modules. Each monolithic detector sub-module includes a scintillator layer, a light-spreading layer, and a photodetector layer. The photodetector layer comprises a two-dimensional array of photodetectors that are arranged in columns and rows. A common printed circuit board is electrically coupled to the two-dimensional array of photodetectors of the plurality of modular one-dimensional arrays of monolithic detector sub-modules of a corresponding modular one-dimensional array. The two-dimensional array of photodetectors can be electrically coupled in a split-row configuration or in a checkerboard configuration. The two-dimensional array of photodetectors can also have a differential readout.

27 Claims, 18 Drawing Sheets

(51) Int. Cl.
*A61B 6/00* (2006.01)
*G01T 1/29* (2006.01)
(52) U.S. Cl.
CPC .......... *A61B 6/4241* (2013.01); *A61B 6/4258* (2013.01); *A61B 6/4266* (2013.01); *A61B 6/4275* (2013.01); *G01T 1/2002* (2013.01); *G01T 1/2006* (2013.01); *G01T 1/2018* (2013.01); *G01T 1/20181* (2020.05); *G01T 1/20184* (2020.05); *G01T 1/20185* (2020.05); *G01T 1/20186* (2020.05); *G01T 1/2985* (2013.01)

(58) Field of Classification Search
CPC ... A61B 6/4258; A61B 6/4266; A61B 6/4275; G01T 1/2006; G01T 1/2018; G01T 1/20181; G01T 1/20182; G01T 1/20184; G01T 1/20185; G01T 1/20186; G01T 1/2002; G01T 1/20187
USPC ............... 378/19, 98.8; 250/370.09, 363.01, 250/363.02, 363.03, 363.04, 363.05, 250/363.08
See application file for complete search history.

(56) References Cited

U.S. PATENT DOCUMENTS

| | | | | |
|---|---|---|---|---|
| 5,991,357 A * | 11/1999 | Marcovici | G01T 1/2018 | 378/149 |
| 6,292,528 B1 * | 9/2001 | Wieczorek | A61B 6/032 | 378/98.2 |
| 6,396,898 B1 * | 5/2002 | Saito | G01N 23/046 | 378/19 |
| 6,426,991 B1 * | 7/2002 | Mattson | A61B 6/032 | 378/19 |
| 6,459,086 B1 * | 10/2002 | Kline | G01T 1/249 | 250/370.01 |
| 6,472,667 B1 * | 10/2002 | Kline | G01T 1/2928 | 250/363.04 |
| 6,510,195 B1 * | 1/2003 | Chappo | G01T 1/2985 | 250/370.09 |
| 6,522,715 B2 * | 2/2003 | Hoffman | G01T 1/2985 | 439/492 |
| 6,586,744 B1 * | 7/2003 | Griesmer | G01T 1/244 | 250/370.15 |
| 6,587,538 B2 * | 7/2003 | Igarashi | H01L 27/14658 | 378/19 |
| 6,621,084 B1 * | 9/2003 | Wainer | G01T 1/244 | 250/370.01 |
| 6,671,345 B2 * | 12/2003 | Vrettos | A61B 6/4233 | 378/19 |
| 6,694,172 B1 * | 2/2004 | Gagnon | A61B 6/4258 | 250/363.02 |
| 6,831,263 B2 | 12/2004 | Skurnik et al. | | |
| 6,917,664 B2 * | 7/2005 | Chappo | G01T 1/1647 | 378/19 |
| 6,952,003 B2 | 10/2005 | Skurnik et al. | | |
| 6,990,176 B2 * | 1/2006 | Sherman | A61B 6/4411 | 378/161 |
| 7,075,089 B2 * | 7/2006 | Pohan | G01T 1/29 | 250/363.04 |
| 7,166,848 B2 * | 1/2007 | El-Hanany | G01T 1/2018 | 250/370.1 |
| 7,177,387 B2 * | 2/2007 | Yasunaga | A61B 6/4035 | 378/149 |
| 7,190,759 B2 * | 3/2007 | Ratzmann | A61B 6/4411 | 378/19 |
| 7,193,208 B1 * | 3/2007 | Burr | G01T 1/2985 | 250/362 |
| 7,202,482 B2 * | 4/2007 | Yokoi | G01T 1/2928 | 250/370.09 |
| 7,217,931 B2 * | 5/2007 | Ueno | G01T 1/2928 | 250/370.09 |
| 7,235,788 B2 * | 6/2007 | Von der Haar | H01L 27/14658 | 250/363.05 |
| 7,235,790 B2 * | 6/2007 | Hoge | G01T 1/2018 | 250/370.11 |
| 7,297,955 B2 * | 11/2007 | Amemiya | G01T 1/2985 | 250/363.04 |
| 7,403,589 B1 * | 7/2008 | Short | G01T 1/2018 | 250/370.11 |
| 7,465,931 B2 * | 12/2008 | Vogtmeier | G01T 1/202 | 378/19 |
| 7,476,864 B2 | 1/2009 | Benlloch Baviera et al. | | |
| 7,489,516 B2 * | 2/2009 | Lacey | A61B 6/032 | 361/740 |
| 7,492,857 B2 * | 2/2009 | Yasunaga | A61B 6/4035 | 378/19 |
| 7,564,940 B2 * | 7/2009 | Mattson | G21K 1/025 | 378/154 |
| 7,582,879 B2 * | 9/2009 | Abenaim | G01T 1/2018 | 250/370.11 |
| 7,586,095 B2 * | 9/2009 | Lutz | A61B 6/035 | 250/370.09 |
| 7,606,346 B2 * | 10/2009 | Tkaczyk | A61B 6/032 | 378/19 |
| 7,705,317 B2 * | 4/2010 | Miyaguchi | H01L 27/14618 | 250/370.11 |
| 8,269,177 B2 * | 9/2012 | Kim | G01T 1/2985 | 250/363.04 |
| 8,350,218 B2 * | 1/2013 | Thon | G01T 1/2002 | 250/361 R |
| 8,648,310 B2 * | 2/2014 | Mollov | G01T 1/2002 | 250/366 |
| 8,723,093 B2 * | 5/2014 | Krymski | H01L 27/14609 | 257/E27.131 |
| 8,779,366 B2 * | 7/2014 | Wieczorek | G01T 1/2018 | 250/363.03 |
| 8,822,941 B2 * | 9/2014 | Ikeda | G01T 1/2018 | 250/361 R |
| 8,829,446 B2 * | 9/2014 | Abenaim | G01T 1/2018 | 250/363.01 |
| 8,937,285 B2 * | 1/2015 | Kim | G01T 1/247 | 250/361 R |
| 9,076,707 B2 | 7/2015 | Harmon | | |
| 9,140,808 B2 * | 9/2015 | Ronda | G01T 1/2018 | |
| 9,207,334 B1 * | 12/2015 | Ito | G01T 1/2018 | |
| 9,354,328 B2 * | 5/2016 | Vogtmeier | G01T 1/2008 | |
| 9,442,200 B2 * | 9/2016 | Watano | G01T 1/2018 | |
| 9,698,181 B2 | 7/2017 | Moldovan et al. | | |
| 9,768,211 B2 | 9/2017 | Harmon | | |
| 10,007,008 B2 * | 6/2018 | Luhta | H01L 27/14661 | |
| 10,222,486 B2 * | 3/2019 | Kim | G01T 1/2018 | |
| 10,288,748 B2 * | 5/2019 | Vogtmeier | A61B 6/037 | |
| 10,488,532 B2 * | 11/2019 | Abenaim | G01T 1/2018 | |
| 10,497,741 B2 * | 12/2019 | Wong | H01L 27/14663 | |
| 10,529,884 B2 | 1/2020 | Harmon | | |
| 10,530,971 B2 * | 1/2020 | Matolin | H04N 9/81 | |
| 11,016,204 B2 * | 5/2021 | Liu | A61B 6/03 | |
| 11,264,422 B2 * | 3/2022 | Harmon | G01S 7/4816 | |
| 2003/0222200 A1 | 12/2003 | Skurnik et al. | | |
| 2011/0210255 A1 | 9/2011 | Kim et al. | | |
| 2012/0175498 A1 | 7/2012 | Krymski | | |
| 2018/0078766 A1 | 3/2018 | Matolin et al. | | |
| 2021/0066382 A1 | 3/2021 | Harmon et al. | | |

OTHER PUBLICATIONS

M. F. Bieniosek et al., "Achieving Fast Timing Performance with Multiplexed SiPMs", Physics in Medicine & Biology, 2016, p. 2879-2892, vol. 61, Institute of Physics and Engineering in Medicine.

M. F. Bieniosek et al., "Analog Filtering Methods Improve Leading Edge Timing Performance of Multiplexed SiPMs", Physics in Medicine & Biology, 2016, p. N427-N440, vol. 61, Institute of Physics and Engineering in Medicine.

H. Choe et al., "Protoype Time-of-Flight PET Utilizing Capacitive Multiplexing Readout Method", Nuclear Inst. and Methods in Physics Research Section A, Mar. 2019, p. 43-49, vol. 921, Elsevier.

(56) References Cited

OTHER PUBLICATIONS

P. W. Cattaneo et al., "Development of high Precision Timing Counter Based on plastic Scintillator with SiPM Readout", IEEE Transactions on Nuclear Science, Feb. 2014, p. 1-11, IEEE.

J. Du et al., "A Simple Capacitive Charge-Division Readout for Position-Sensitive Solid-State Photomultiplier Arrays", NIH Public Access Author Manuscript, Oct. 2013, p. 1-24, vol. 60 Issue 5, IEEE.

M. D'Incecco et al., "Development of a Novel Single-Channel, 24cm$^\vee$2, SiPM-based, Cryogenic Photodetector", IEEE Transactions on Nuclear Science, 2018, p. 591-596,vol. 65 Issue 1, IEEE.

L. H. C. Braga et al., "A Fully Digital 8×16 SiPM Array for PET Applications With Per-Pixel TDCs and Real-Time Energy Output", IEEE Journal of Solid-State Circuits, Jan. 2014, p. 301-314, vol. 49, IEEE.

H. Park et al., "Hybrid Charge Division Multiplexing Method for Silicon Photomultiplier Based PET Detectors", IOP Science, May 2017, p. 4390-4405, vol. 62 No. 11, Institute of Physics and Engineering in Medicine.

K. Leki et al., "Large-Area MPPC with Enhanced VUV Sensitivity for Liquid Xenon Scintillation Detector", Nuclear Instruments and Methods in Physics Research Section A: Accelerators, Spectrometers, Detectors and Associated Equipment, Feb. 2019, p. 1-10, vol. 925, Elsevier.

G. B. Ko et al., "Development of a Front-end Analog Circuit for Multi-Channel SiPM Readout and Performance Verification for Various PET Detector Designs", Nuclear Instruments and Methods in Physic Research, 2013, p. 38-44, vol. 703, Elsevier.

S. I. Kwon et al., "Signal Encoding Method for a Time-of-Flight PET Detector Using a Silicon Photomultiplier Array", Nuclear Instruments and Methods in Physics Research A, 2014, p. 39-45, vol. 761, Elsevier.

M. F. Bieniosek et al., "A Multiplexed TOF and DOI Capable PET Detector Using a Binary Position Sensitive Network", Phys Med Biol, Nov. 2016, p. 1-21, vol. 61 No. 21, Institute of Physics and Engineering in Medicine.

J. W. Cates et al., "Highly Multiplexed Signal Readout for a Time-of-Flight Positron Emission Tomography Detector Based on Silicon Photomultipliers", J. Med. Imag., 2017, p. 1-9, vol. 4 No. 1.

M. Janecek et al., "A High-Speed Multi-Channel Readout for SSPM Arrays", IEEE Transactions on Nuclear Science, 2012, p. 13-18, vol. 59 No. 1, IEEE.

J. W. Cates et al., "Evaluation of a clinical TOF-PET detector design that achieves ≤100 ps coincidence time resolution", Phys Med Biol., 2018, p. 1-30, vol. 63 No. 11.

S. Moehrs et al., "A Small-Animal PET Design Using SiPMs and Anger Logic with Intrinsic DOI", IEEE Symposium Conference Record Nuclear Science, 2004, p. 3475-3479, vol. 6, IEEE.

A. Gonzalez-Montoro et al., "Detector block performance based on a monolithic LYSO crystal using a novel signal multiplexing method", Nuclear Instruments and Methods in Physics Research Section A: Accelerators, Spectrometers, Detectors and Associated Equipment, 2018, p. 372-377.

P. Peng et al., "Compton PET: a layered structure PET detector with high performance", Physics in Medicine & Biology, 2019, pp. 1-16, vol. 64 No. 10, Institute of Physics and Engineering in Medicine.

V. Ilisie et al., "Building blocks of a multi-layer PET with time sequence photon interaction discrimination and double Compton camera", Nuclear Inst. and Methods in Physics Research, 2018, pp. 1-28, vol. 895, Elsevier.

D. Schaart et al., "A novel, SiPM-array-based, monolithic scintillator detector for PET", Physics in Medicine and Biology, 2009, pp. 3501-3512, vol. 54, Institute of Physics and Engineering in Medicine.

J. Yeol Yeom et al., "Side readout of long scintillation crystal elements with digital SiPM for TOF-DOI PET", Med. Phys., 2014, pp. 1-9, vol. 41 No. 12, American Association of Physicists in Medicine.

A. Mäkynen et al., "Linear and sensitive CMOS position-sensitive photodetector", Electronics Letters, Jun. 11, 1998, vol. 34 No. 12.

A. Mäkynen et al., "High accuracy CMOS position-sensitive photodetector (PSD)", Electronics Letters, Jan. 16, 1997, vol. 33 No. 2.

A. Mäkynen et al., "High Performance CMOS position-sensitive photodetectors (PSDs)", 1998.

D'Incecco et al., "Development of a novel single-channel, 24 cm$^2$, SiPM-based, cryogenic photodetector", Nov. 3, 2017.

* cited by examiner

MODULAR PET DETECTOR COMPRISING A PLURALITY OF MODULAR ONE-DIMENSIONAL ARRAYS OF MONOLITHIC DETECTOR SUB-MODULES

CROSS-REFERENCE TO RELATED APPLICATIONS

This application claims priority to U.S. Provisional Application No. 62/963,656, filed on Jan. 21, 2020, titled "Modular Pet Detector," and to U.S. Provisional Application No. 63/055,027, filed on Jul. 22, 2020, titled "Modular Pet Detector," which are hereby incorporated by reference.

STATEMENT REGARDING FEDERALLY SPONSORED RESEARCH

This invention was made with U.S. government support under Grant No. R43MH115637, awarded by the National Institutes of Health. The U.S. government has certain rights in the invention.

TECHNICAL FIELD

This application relates generally to positron emission tomography (PET) detectors.

BACKGROUND

PET is a well-known technology of detecting molecular activity in humans and animals. In PET, a radioactive tracer is injected into bloodstream. Typical tracers are labeled with radioactive F-18. Glucose labeled with F-18, fluorodeoxyglucose (FDG), is typically used to detect the activity of tissue. More FDG intake means the tissue is more active.

F-18 emits positrons which decay into two counter-propagating (anti-parallel) 511 keV gamma rays. Detectors on opposite sides of the region being imaged detect these two gamma rays in coincidence. Coincident events indicate that the radioactive F-18 is within a line-of-response (LOR) between the two detectors. Time-of-flight (TOF) can be used to localize the position along the LOR.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to a gamma-ray detector comprising: a plurality of modular one-dimensional arrays of monolithic detector sub-modules. Each monolithic detector sub-module comprises a scintillator layer; a light-spreading layer mounted on the scintillator layer; and a photodetector layer mounted on the light-spreading layer, the photodetector layer comprising a two-dimensional array of photodetectors that are arranged in columns and rows. The detector further comprises a plurality of common printed circuit boards (PCBs), each common PCB electrically coupled to the photodetectors of the monolithic detector sub-modules of a corresponding modular one-dimensional array. For each monolithic detector sub-module: the photodetectors on a first side of each row are electrically coupled to a corresponding first side output line, and the photodetectors on a second side of each row are electrically coupled to a corresponding second side output line.

In one or more embodiments, the light-spreading layer comprises a spacer layer. In one or more embodiments, in each monolithic detector sub-module: the photodetectors on the first side of each row are electrically coupled in series, and the photodetectors on the second side of each row are electrically coupled in series. In one or more embodiments, in each monolithic detector sub-module: the photodetectors on the first side of each row are configured to output a first differential signal, and the photodetectors on the second side of each row are configured to output a second differential signal.

In one or more embodiments, in each monolithic detector sub-module: the photodetectors on the first side of each row are electrically coupled in parallel with each other, and the photodetectors on the second side of each row are electrically coupled in parallel with each other. In one or more embodiments, in each monolithic detector sub-module: the photodetectors on the first side of each row are configured to output a first differential signal, and the photodetectors on the second side of each row are configured to output a second differential signal.

In one or more embodiments, a number of the photodetectors on the first side of each row is equal to a number of the photodetectors on the second side of each row. In one or more embodiments, a first end of each common PCB is attached to a first support ring, and a second end of each common PCB is attached to a second support ring. In one or more embodiments, the first support ring includes electrical connections that are electrically coupled to each common PCB.

Another aspect of the invention is directed to a gamma-ray detector comprising a plurality of modular one-dimensional array of monolithic detector sub-modules. Each monolithic detector sub-module comprises a scintillator layer; a light-spreading layer mounted on the scintillator layer; and a photodetector layer mounted on the light-spreading layer. The photodetector layer comprises a two-dimensional array of photodetectors that are arranged in columns and rows and comprise: horizontal arrays of HA photodetectors, the HA photodetectors in each horizontal array electrically coupled in series to each other; and vertical arrays of VA photodetectors, the VA photodetectors in each vertical array electrically coupled in series to each other. Each row includes all of the HA photodetectors from only one of the horizontal arrays and only one VA photodetector from each of a plurality of different vertical arrays, each column includes all of the VA photodetectors from only one of the vertical arrays and only one HA photodetector from each of a plurality of different horizontal arrays, and the HA and VA photodetectors are arranged in an alternating sequence to form a photodetector grid. The detector further comprises a plurality of common printed circuit boards (PCBs), each common PCB electrically coupled to the photodetectors of the monolithic detector sub-modules of a corresponding modular one-dimensional array. For each monolithic detector sub-module: an HA output line is electrically coupled to each horizontal array of HA photodetectors, and a VA output line is electrically coupled to each vertical array of VA photodetectors.

In one or more embodiments, in each monolithic detector sub-module: each HA output line is configured to output a first differential signal, and each VA output line is configured to output a second differential signal. In one or more embodiments, a first end of each common PCB is attached to a first support ring, and a second end of each common PCB is attached to a second support ring. In one or more embodiments, the first support ring includes electrical connections that are electrically coupled to each common PCB.

Another aspect of the invention is directed to a gamma-ray detection system. The system includes a gamma-ray detector comprising: a plurality of modular one-dimensional arrays of monolithic detector sub-modules. Each monolithic detector sub-module comprises a scintillator layer; a light-spreading layer mounted on the scintillator layer; and a photodetector layer mounted on the light-spreading layer, the photodetector layer comprising a two-dimensional array of photodetectors that are arranged in columns and rows. The detector further comprises a plurality of common printed circuit boards (PCBs), each common PCB electrically coupled to the photodetectors of the monolithic detector sub-modules of a corresponding modular one-dimensional array. For each monolithic detector sub-module: the photodetectors on a first side of each row are electrically coupled to a corresponding first side output line, and the photodetectors on a second side of each row are electrically coupled to a corresponding second side output line. The system also includes a computer in electrical communication with the common PCBs, the computer configured to determine a first position of an incident gamma ray with respect to a first axis by determining: a highest-magnitude signal row based on a sum of a respective first output magnitude of the first side of each row and a respective second output magnitude of the second side of each row, and a relative position of the incident gamma ray within the highest-magnitude signal row using the respective first output magnitude of the first side of the highest-magnitude signal row and the respective second output magnitude of the second side of the highest-magnitude signal row.

In one or more embodiments, the computer is further configured to determine: a second-magnitude signal row based on a sum of a respective first output magnitude of the first side of each row and a respective second output magnitude of the second side of each row, and a relative second position of the incident gamma ray using a magnitude of the highest-magnitude signal row and a magnitude of the second-highest-magnitude signal row, the relative second position determined with respect to a second axis that is orthogonal to the first axis and that lies in a major plane defined by the photodetector layer. In one or more embodiments, the computer is further configured to determine: a third-highest-magnitude signal row based on the sum of the respective first output magnitude of the first side of each row and the respective second output magnitude of the second side of each row, and a relative third position of the incident gamma ray using the magnitude of the highest-magnitude signal row, the magnitude of the second-highest-magnitude signal row, and the magnitude of the third highest-magnitude signal row, the relative third position determined with respect to a third axis that is orthogonal to the first and second axes. In one or more embodiments, the relative third position is determined by fitting the magnitude of the highest-magnitude signal row, the magnitude of the second-highest-magnitude signal row, and the magnitude of the third highest-magnitude signal row to a curve.

Yet another aspect of the invention is directed to a gamma-ray detection system. The system includes a gamma-ray detector comprising a plurality of modular one-dimensional array of monolithic detector sub-modules. Each monolithic detector sub-module comprises a scintillator layer; a light-spreading layer mounted on the scintillator layer; and a photodetector layer mounted on the light-spreading layer. The photodetector layer comprises a two-dimensional array of photodetectors that are arranged in columns and rows and comprise: horizontal arrays of HA photodetectors, the HA photodetectors in each horizontal array electrically coupled in series to each other; and vertical arrays of VA photodetectors, the VA photodetectors in each vertical array electrically coupled in series to each other. Each row includes all of the HA photodetectors from only one of the horizontal arrays and only one VA photodetector from each of a plurality of different vertical arrays, each column includes all of the VA photodetectors from only one of the vertical arrays and only one HA photodetector from each of a plurality of different horizontal arrays, and the HA and VA photodetectors are arranged in an alternating sequence to form a photodetector grid. The detector further comprises a plurality of common printed circuit boards (PCBs), each common PCB electrically coupled to the photodetectors of the monolithic detector sub-modules of a corresponding modular one-dimensional array. For each monolithic detector sub-module: an HA output line is electrically coupled to each horizontal array of HA photodetectors, and a VA output line is electrically coupled to each vertical array of VA photodetectors. The system also includes a computer in electrical communication with the common PCBs, the computer configured to determine a first position of an incident gamma ray with respect to a first axis by determining: the vertical arrays having a VA power output greater than a threshold power output, and a relative first position of the incident gamma ray using the VA power output(s) of the vertical arrays that are greater than the threshold power output.

In one or more embodiments, the computer is further configured to determine: the horizontal arrays having an HA power output greater than the threshold power output, and a relative second position of the incident gamma ray using the VA power output(s) of the vertical arrays that are greater than the threshold power output, the relative second position determined with respect to a second axis that is orthogonal to the first axis, the first and second axes parallel to the rows and columns, respectively. In one or more embodiments, the computer is further configured to determine a third position of the incident gamma ray using a variance of the HA and VA power outputs that are greater than the threshold power output.

Another aspect of the invention is directed to a gamma-ray detector comprising: a plurality of arrays of monolithic detector sub-modules. Each monolithic detector sub-module comprises a scintillator layer; a light-spreading layer mounted on the scintillator layer; and a photodetector layer mounted on the light-spreading layer, the photodetector layer comprising a two-dimensional array of photodetectors that are arranged in columns and rows; a plurality of common printed circuit boards (PCBs), each common PCB electrically coupled to the photodetectors of the monolithic detector sub-modules of a corresponding modular one-dimensional array; and first and second support rings. For each monolithic detector sub-module: the photodetectors on a first side of each row are electrically coupled to a corresponding first side output line, the photodetectors on a second side of each row are electrically coupled to a corresponding second side output line, a first end of each common PCB is attached to the first support ring, a second end of each common PCB is attached to the second support ring. The plurality of modular one-dimensional sub-modules forms an inner cylinder and an outer cylinder, the inner cylinder concentrically disposed within the outer cylinder.

In one or more embodiments, the inner and outer cylinders are spaced apart to form an air gap therebetween. In one or more embodiments, the plurality of modular one-dimensional arrays in the outer cylinder are positionally offset with respect to the plurality of modular one-dimensional arrays in the inner cylinder. In one or more embodiments, a central axis passes through a center of the inner and outer cylinders, a first radial axis passes through a first gap between adjacent monolithic detector sub-modules in a first inner modular one-dimensional array in the inner cylinder, the first radial axis orthogonal to the central axis, and the first radial axis passes through a first outer monolithic detector sub-module in a first outer modular one-dimensional array in the outer cylinder.

In one or more embodiments, a second radial axis passes through a second gap between adjacent monolithic detector sub-modules in a second outer modular one-dimensional array in the outer cylinder, the second radial axis orthogonal to the central axis, and the second radial axis passes through a first inner monolithic detector sub-module in a second inner modular one-dimensional array in the inner cylinder. In one or more embodiments, a third radial axis passes through a first inactive edge between adjacent photodetectors in a second inner monolithic detector sub-module in a third inner modular one-dimensional array in the inner cylinder, the third radial axis orthogonal to the central axis, and the third radial axis passes through an active photodetector in a second outer monolithic detector sub-module in a third outer modular one-dimensional array in the outer cylinder. In one or more embodiments, a fourth radial axis passes through a second inactive edge between adjacent photodetectors in a third outer monolithic detector sub-module in a fourth outer modular one-dimensional array in the outer cylinder, the fourth radial axis orthogonal to the central axis, and the fourth radial axis passes through an active photodetector in a third inner monolithic detector sub-module in a fourth inner modular one-dimensional array in the inner cylinder.

BRIEF DESCRIPTION OF THE DRAWINGS

For a fuller understanding of the nature and advantages of the present concepts, reference is made to the detailed description of preferred embodiments and the accompanying drawings.

DETAILED DESCRIPTION

Figure 1:
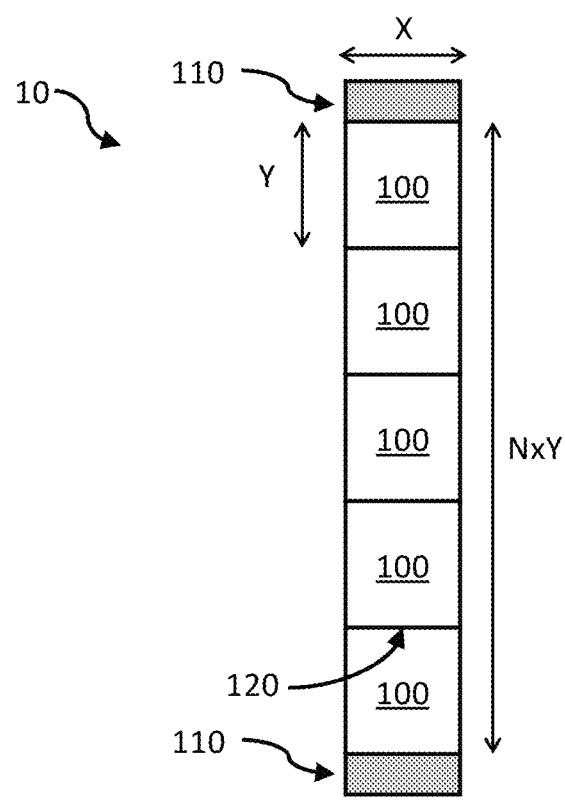
FIG. 1 is a block diagram of a thin-slab detector module according to an embodiment.

FIG. 1 is a block diagram of a thin-slab detector module 10 according to an embodiment. The thin-slab detector module 10 includes a one-dimensional array of N monolithic detector sub-modules 100 assembled side-by-side. The detector sub-modules 100 are spaced apart that an inactive gap 120 formed between adjacent detector sub-modules 100. Each detector sub-module 100 has a width (e.g., "X" in the Cartesian coordinate system) and a length (e.g., "Y" in the Cartesian coordinate system). The array of N detector sub-modules 100 has an overall length of N×Y. Each sub-module 100 is electrically coupled to (e.g., mounted on) a common printed circuit board (PCB) 110 which provides an electrical interconnection between each sub-module 100 and external circuitry (e.g., electrical leads to a computer) to readout the signal generated by the thin-slab detector module 10. The common PCB 110 can be located behind (in the Cartesian Z direction) the monolithic detector sub modules 100 so as to also provide mechanical/physical support for the sub-module array. In some embodiments, the common PCB 110 can include readout electronics (e.g., preamplifiers, timing digitizers, amplitude digitizers, position-sensing digitizers, voltage supplies, and/or other readout electronics).

The array of N detector sub-modules 100 can have any number of sub-modules 100. In an embodiment, the array has 6-12 sub-modules 100. In a preferred embodiment, the array has 8 sub-modules 100. A technical advantage of the thin-slab detector module 10 is that it is easy to manufacture, low cost, and easy and inexpensive to replace or repair.

In some embodiments, adjacent or neighboring detector sub-modules 100 are completely independent. For example, a reflective layer or a light-absorbing layer can be placed between each detector sub-module 100, such as in gap 120, to confine the incident light to each detector sub-modules 100. The reflective layer may be a specular reflector (e.g., aluminum foil) and/or a diffusive reflector (e.g., PTFE (e.g., Teflon®) tape). A light-absorbing layer can include a dark material such as black paint (e.g., carbon black paint).

In some embodiments, the thin-slab detector module 10 can be configured to allow light sharing between adjacent or neighboring detector sub-modules. Light sharing can be achieved by (a) using a single, long photodetector layer 200 with dimensions of X×(N×Y)×Z1; (b) gluing the detector sub-modules 100 together using a high-refractive-index glue; (c) using a single, long light-spreading layer 210 with dimensions of X×(N×Y)×Z2; (d) using a single, long scintillator layer 220 with dimensions of X×(N×Y)×Z3; or (e) a combination of any of (a)-(d). With respect to embodiment (b), preferably the refractive index of the glue would match the refractive index of the scintillators. In practice, high refractive index glues are difficult to obtain, so use as high an index as is available (e.g., use glue with a refractive index of about 1.6 for a scintillator layer 220 having a refractive index of about 1.8). For example, the refractive index of the glue can be within about 20% of the refractive index of the scintillator layer 220. In the case of embodiment (b), the optional reflective layers would not be used. As used herein, "about" means plus or minus 10% of a given value.

A technical advantage of sharing light between the adjacent or neighboring detector sub-modules 100 is that it reduces edge effects (e.g., as described below). The array of photodetector elements 205 may similarly be reconfigured to detect light from the entire X×(N×Y) face area of the light sharing layer, since all of sub-modules in the thin-slab detector 60 have been merged. The array of photodetector elements 205 can be configured to be a single, large position sensitive photodetector (with total area of X×(N×Y)), or can be configured into an arbitrary array of position sensitive photodetectors within this total area. One particularly useful reconfiguration of photodetector elements 205 would be to reconfigure them into one dimensional arrays of photodetector elements, where the Y dimension matches the Y dimension of a single photodetector element 205, and the X dimension spans X dimension of layer 220. Position sensing in one dimension only is often more accurate and requires fewer corrections for nonlinearity in the photocurrent splitting. Position sensing in the Y dimension would be achieved by digitally combining the digitized outputs of the array of one-dimensional position sensing photodetectors to estimate the centroid position in the Y dimension. This would enable a one-dimensional measurement of the variance in the beam (i.e., beam diameter) in the Y direction. The resulting signals would be: X-centroid (using position sensing in the X dimension), Y-centroid (using position sensing in the Y dimension), and Y-variance (using the spread in the Y dimension to form estimates of the spot size diameter). The Y variance can be used to refine the estimate of the depth of interaction (DOI) of the Gamma ray, which can improve timing resolution, improve energy resolution (e.g., since saturation effects can be calibrated if DOI is known), and/or can allows thicker crystals to be used in the scintillator layer 220, reducing the number of stacked long-slab modules.

Figure 2:
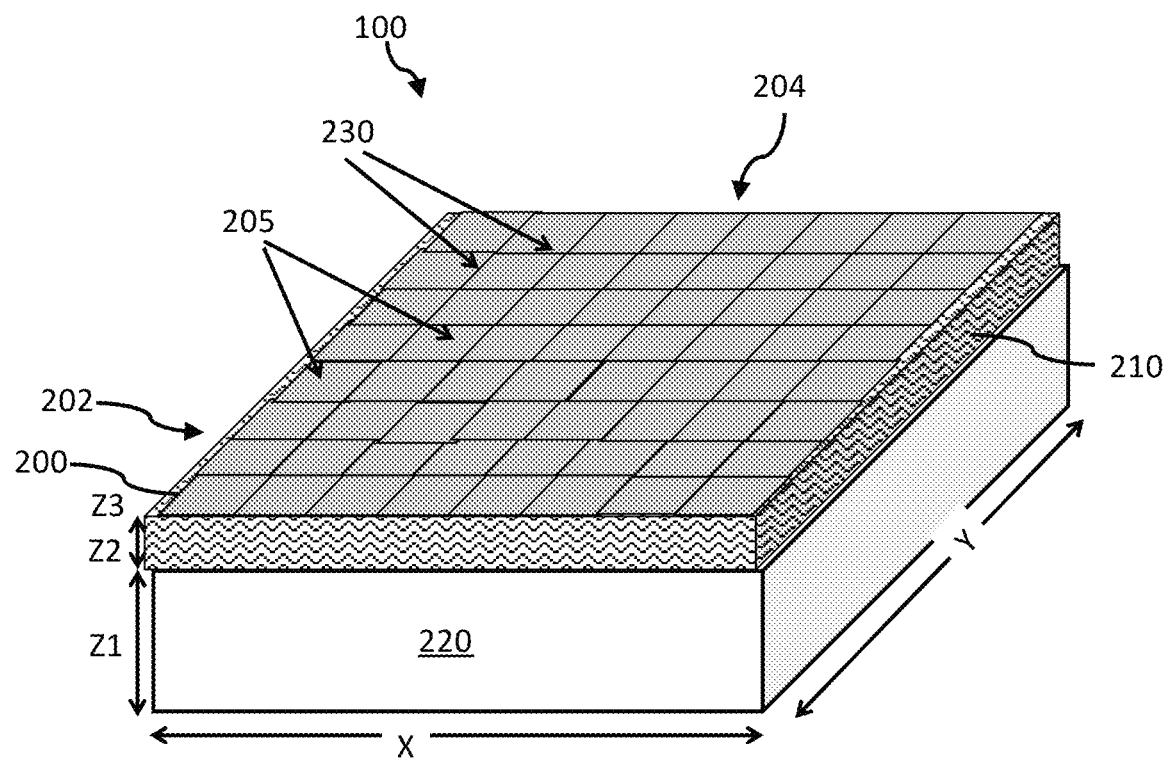
FIG. 2 is a block diagram of a representative detector sub-module according to an embodiment.

FIG. 2 is a block diagram of a representative detector sub-module 100 according to an embodiment. The detector sub-module 100 includes a photodetector layer 200, a light-spreading layer 210, and a scintillator layer 220 that are arranged in a stacked configuration. The light-spreading layer 210 can be a spacer layer in some embodiments. The photodetector layer 200 is disposed or mounted on the light-spreading layer 210, which is disposed or mounted on the scintillator layer 220.

The photodetector layer 200 includes a plurality of photodetectors 205, which can be disposed in a two-dimensional array. The two-dimensional array can include rows 202 and columns 204 of photodetectors 205. Each photodetector 205 can be or can comprise a semiconductor photodetector, such as a PIN photodiode, an avalanche photodiode, a silicon photomultiplier (SiPM), an avalanche photodiode, or a photomultiplier chip. Examples of avalanche photodiodes are disclosed in U.S. Pat. No. 9,076,707, titled "Integrated Avalanche Photodiode Arrays," U.S. Pat. No. 9,768,211, titled "Integrated Avalanche Photodiode Arrays," and U.S. Pat. No. 10,529,884, titled "Virtual Negative Bevel and Methods of Isolating Adjacent Devices," which are hereby incorporated by reference.

The sub-module 100 can have X, Y, and Z dimensions in the Cartesian coordinate system. The scintillator layer 220 has a thickness (Z1) and about the same X and Y dimensions as the photodetector layer 200. In some embodiments, $Z1 \ll X, Y$ (for example, $Z1<X/2$ and/or $Z1<Y/2$), where X and Y are the respective dimensions of sub-module 100. In another example, $Z1 \ll X, Y$ (for example, $X/10<Z1<X/2$ and/or $Y/10<Z1<Y/2$). Example dimensions are X=Y=about 32 mm and Z1=about 3 mm. In other embodiments, Z1 can be in a range of about 3 mm to about 10 mm. Example materials used for the scintillator layer 220 include thallium-doped sodium iodide (NaI(Tl)), cesium iodide (CsI), Bismuth Germanate (BGO, $Bi_4Ge_3O_{12}$), LYSO ($Lu_{1.8}Y_{0.2}SiO_5$:Ce), and LSO (Lutetium Oxyorthosilicate—$Lu_2SiO_5$:Ce).

The light-spreading layer 210 has a thickness (Z2) selected to allow sufficient light spreading within the light-spreading layer 210 so as to minimize saturation of the photodetectors 205. For example, without light-spreading layer (i.e., Z2=0 mm), gamma rays may be absorbed directly adjacent to the photodetector layer 200, causing a large number of photons to intersect a very small region of the photodetector layer 200, resulting in saturation. Typical Z2 dimensions are about 0.1 mm<Z2<about 2×Z1. An example Z2 dimension is about 1 mm. Ideally, the light-spreading layer 210 has an index of refraction that is a close match to the index of refraction of scintillator layer 200 (e.g., within about 5% to about 25%), so as to minimize Fresnel reflection of scintillation photons at the interface between the scintillator layer 200 and the light-spreading layer 210. A typical index of refraction for the scintillator layer 200 is 1.81, though the index of refraction can range from about 1.5 to about 2.2, including about 1.7, about 1.9, about 2.1, and any value or range between any two of the foregoing indexes of refraction. Because the index of refraction often varies as a function of the optical wavelength, it is desirable to match the index of refraction for the wavelengths of the scintillation photons. In addition, it is desirable for the light-spreading layer 210 to be highly-transparent (low absorption of the scintillation photons) and to have low absorption for the gamma rays, since gamma ray absorption in the light-spreading layer 210 generally results in a missed detection event. This typically means that the light-spreading layer 210 includes optically-transparent materials with a low density and which incorporate low atomic number elements. Typically, the light-spreading layer 210 includes organic materials such as acrylics, thermoplastics, and/or other polymers. Other materials such as transparent silica gels and low-density optical glass may also be used for the light-spreading layer 210. The light-spreading layer 210 typically has the same X and Y dimensions as the photodetector layer 200. The light-spreading layer 210 can be formed only of or can comprise $Al_2O_3$ (alumina and/or sapphire), gallium oxide ($Ga_2O_3$), and/or silicon nitride ($Si_3N_4$).

The thickness of the photodetector layer 200 corresponds to or is equal to the thickness (Z3) of the diode of each photodetector 205, which is typically in the range of about 10 microns to about 1,000 microns, including about 250 microns, about 500 microns, about 750 microns, and any value or range between any two of the foregoing thicknesses.

The overall dimensions of the sub-module 100 are X×Y×Ztotal, where Ztotal=Z1+Z2+Z3. Accordingly, the overall dimensions of the array of N monolithic detector sub-modules 100 in the thin-slab detector module 10 are X×(N×Y)×Ztotal. The common PCB 110 has dimensions of approximately X×(N×Y)×Z4 where Z4 is the thickness of common PCB 110. It is noted that the Y dimension of common PCB 110 can be slightly greater than (N×Y) to provide additional PCB material on either side of the first and last detector sub-modules 100 in the thin-slab detector module 10 (e.g., as illustrated in FIG. 1). This additional PCB material can be used for physical mounting and interconnection of thin-slab detector module 10 to a physical support structure and/or interconnect wiring structure.

Alternative designs can replace common PCB 110 with a flex circuit for the electrical connections and use other parts for the physical support sub-module array. In this case, the physical support can be or include one or more of the following (a) the scintillator material itself (scintillator layer 220), with approximate dimensions of X×(N×Y)×Z1; (b) the light-spreading layer 210 with approximate dimensions of X×(N×Y)×Z2; and/or another support layer such as a thermal management layer with approximate dimensions of X×(N×Y)×Z5, where Z5 is the thickness of the thermal management layer. The thermal management layer can have high thermal conductivity.

Preferably, the materials and thickness of the light-spreading layer 210, photodetector layer 200, common PCB 110, and/or other support layer have minimal gamma ray absorption such that less than $\frac{1}{10}$th of the incident gamma rays are absorbed in these layers. This can partly be achieved by making Z2, Z3, Z4, and Z5 (when a thermal management layer is included) as thin as possible (given other requirements), and partly by using lightweight, low-density, low-effective-atomic-number (low-Z) materials.

Figure 3:
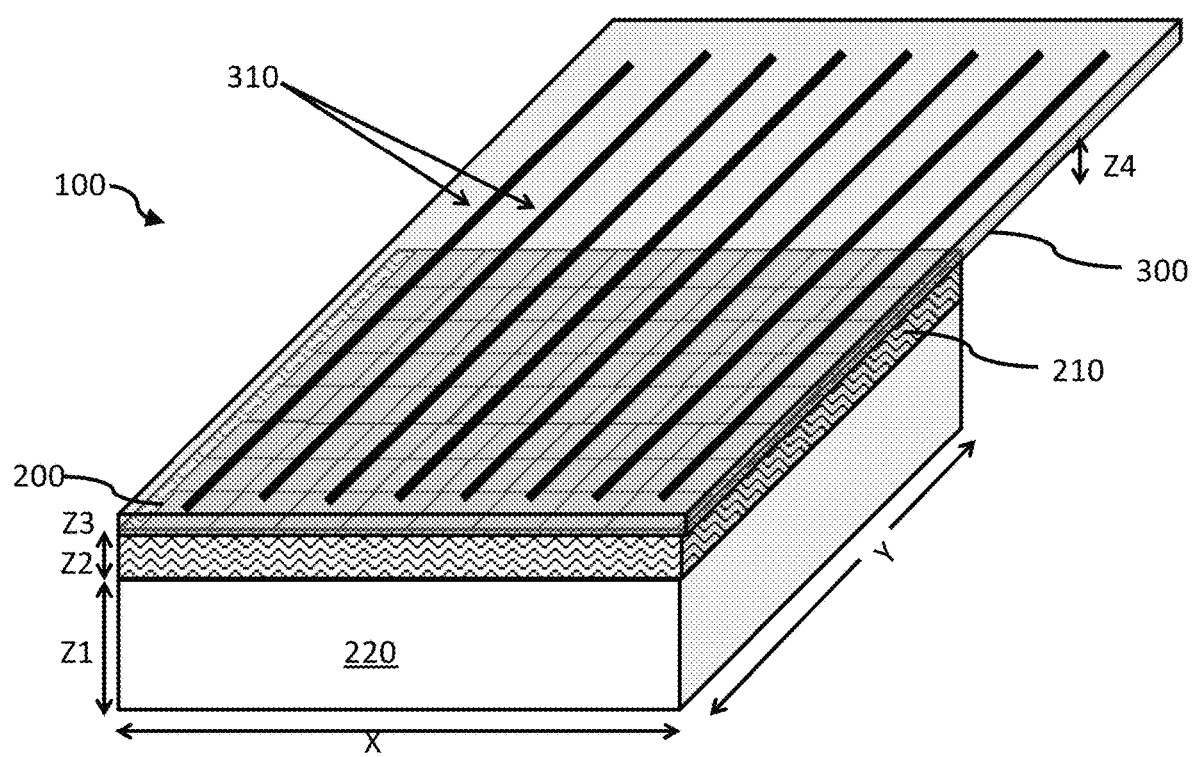
FIG. 3 is a block diagram that illustrates a common PCB disposed or mounted on the representative detector sub-module illustrated in FIG. 2.

A common PCB 300 is disposed or mounted on the photodetector layer 200 as illustrated in FIG. 3. The common PCB 300 includes interconnects or wiring 310 to electrically couple the photodetectors 205 to an external device. Common PCB 300 can be the same as or different than common PCB 110.

Position sensitivity can be achieved using a number of techniques, such as an individual readout of each element of the photodetector array, an Anger Logic position-sensing readout using charge sharing to split the detected signal between X-position and Y-position readouts (e.g., as described in U.S. patent application Ser. No. 16/557,149 ("the '149 application"), titled "Scalable Position-Sensitive Photodetector Device," filed on Aug. 30, 2019, which is hereby incorporated by reference), a checkerboard readout (e.g., as described in the '149 application), or another position-sensing circuit/readout (e.g., as known in the art).

Figure 4:
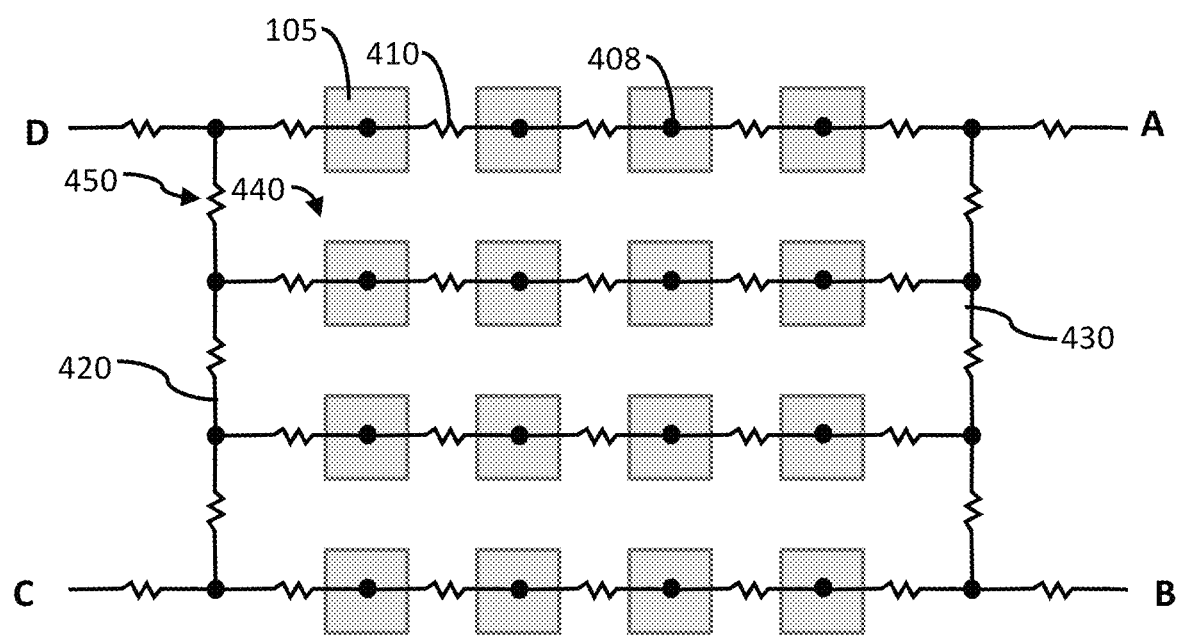
FIG. 4 illustrates Anger logic circuit connections of photodetectors with resistive mesh connections.

An example of a conventional Anger logic circuit connections includes resistive mesh connections of photodetectors 105 with current photocurrent outputs A-D as illustrated in FIG. 4. All the cathodes 408 (or alternatively all the anodes) of the photodetectors 105 are connected in common. The anodes 408 (or cathodes) of photodetectors 105 are connected in rows 440 where a resistor 410 is connected in series between the anode 408 (or cathode) of each photodetector 105. The rows 440 of the photodetector array are connected to adjacent rows 440 at both ends with output lines 420, 430 using another resistor 450 between each row 740. The outputs A-D are at the corners of the array with an additional resistor 450 connected in series between each output A-D and the respective termination of the output lines 420, 430. The photodetector current is divided between each of the four corners in inverse proportion to the total resistance between the activated photodetector 105 and the corner contact (e.g., as in a resistive divider).

Figure 5:
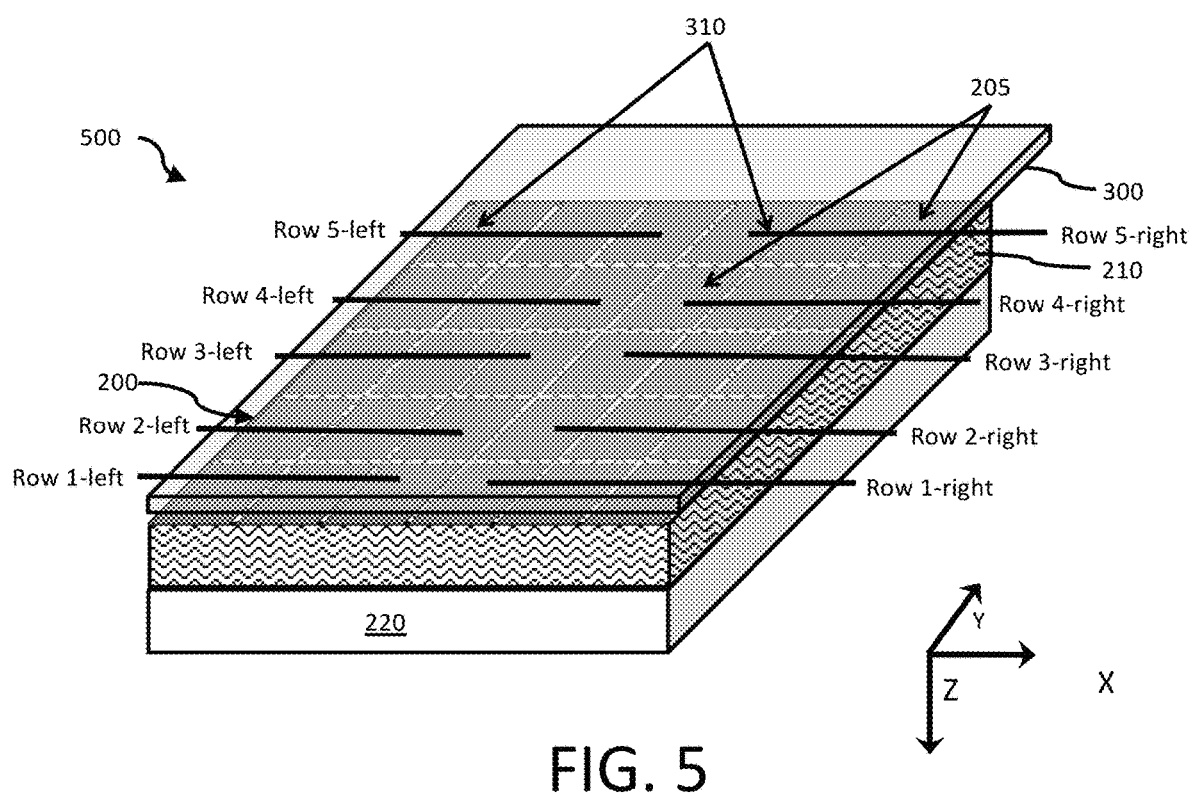
FIG. 5 is a block diagram of an example detector sub-module for a thin-slab detector having one-dimensional array split-row connections of photodetectors.

An example of a detector sub-module 500 for a thin-slab detector having one-dimensional array split-row connections of photodetectors 205 is illustrated in FIG. 5. The sub-module 500 is the same as sub-module 100 illustrated in FIG. 3 except that in sub-module 500 the wiring 310 of PCB 300 electrically connects the photodetectors 705 in multiple one-dimensional arrays (rows 1-5). In some embodiments, sub-module 500 can include an array of one-dimensional arrays (e.g., M×N). Each one-dimensional array is configured to have a left side and a right side that are not electrically coupled to each other (e.g., split rows). For example, the wiring 310 for row 1 is configured with a row 1-left side and a row 1-right side. Rows 3-5 are wired in the same manner with respective left and right sides.

The photodetectors 205 on each side of each row can be electrically coupled in parallel or in series with each using wiring 310. The photodetectors 205 in each row and side are preferably electrically coupled identically (e.g., all parallel or serial connections). The photodetectors 205 in a given row and side (e.g., row 1-left) are electrically isolated from the other photodetectors 205. For example, the photodetectors in row 1-left are not electrically coupled to the photodetectors 205 in row 1-right or in any other row or side.

Figure 7:
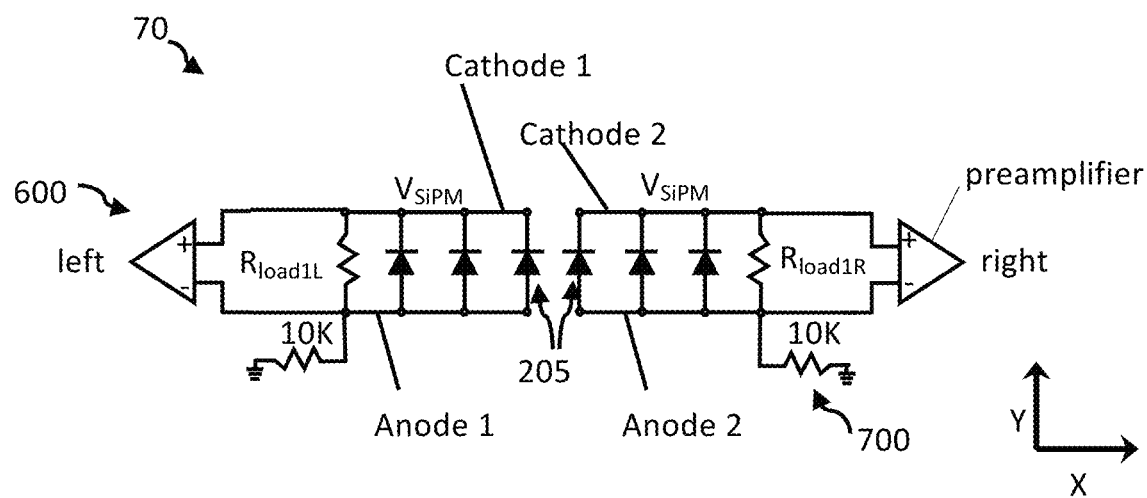
FIG. 7 is an alternative embodiment of the schematic circuit diagram illustrated in FIG. 6.
Figure 8:
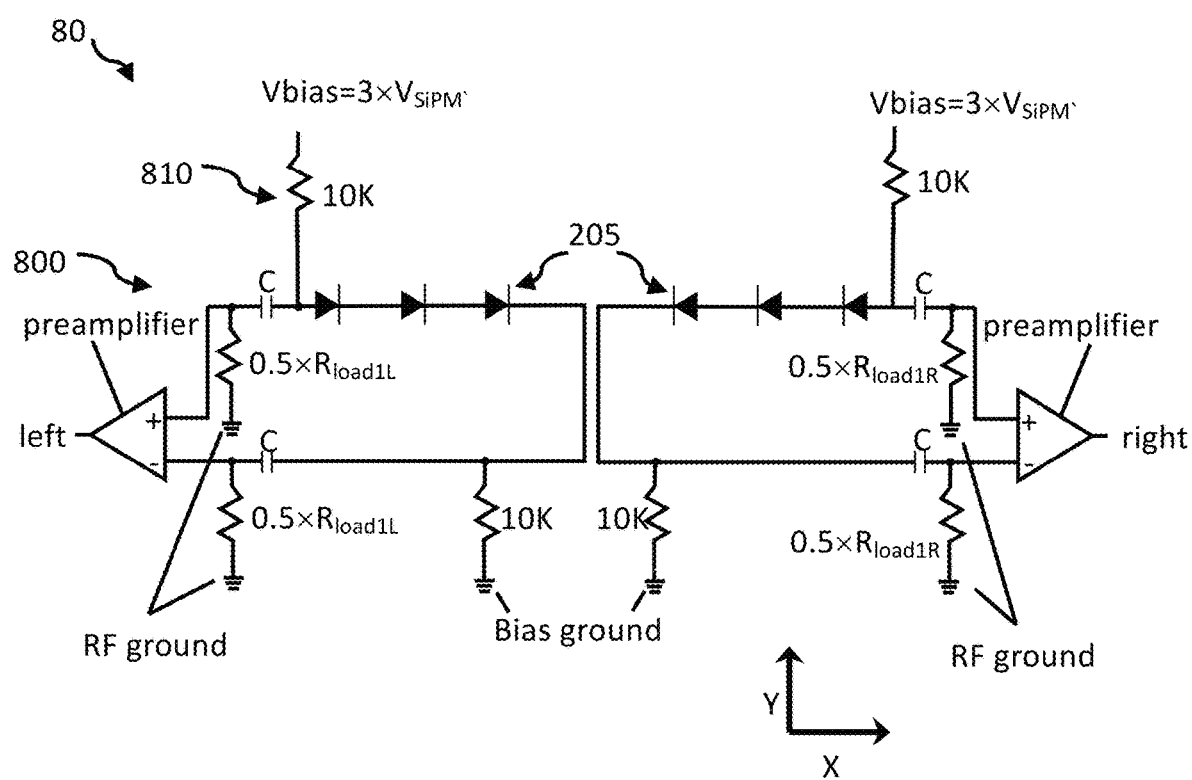
FIG. 8 is a schematic circuit diagram of a representative row of photodetectors in detector sub-module according to a second embodiment.

Advantages of electrically connecting the photodetectors 205 in series (e.g., as illustrated in FIG. 8) include that the signal propagates through the serial-connected circuit faster compared to the parallel-connected circuit (e.g., illustrated in FIGS. 6 and 7), which requires time and energy to charge the capacitor in each photodetector 205. In addition, the output voltage signal in the serial-connected circuit has a relatively higher amplitude and shorter duration compared to the output signal for the same/equivalent input signal in the parallel-connected circuit. The advantages of the series-connected circuit are due, at least in part, to the energy needed to charge the capacitors in each photodetector 205 in the parallel-connected circuit, which does not occur in the serial-connected circuit.

Figure 6:
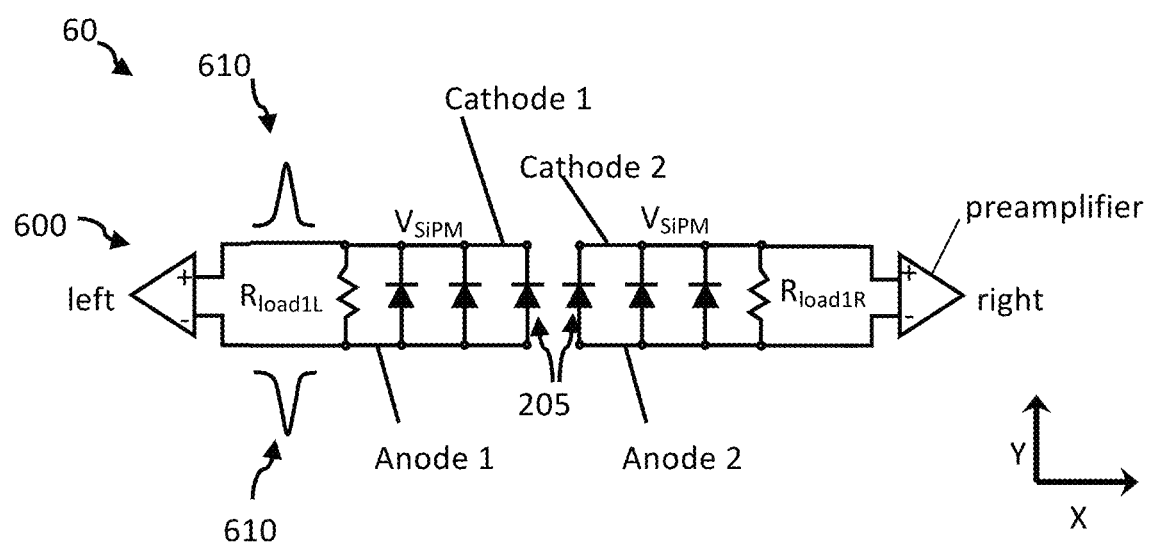
FIG. 6 is a schematic circuit diagram of a representative row of photodetectors in detector sub-module according to a first embodiment.

FIG. 6 is a schematic circuit diagram 60 of a representative row 600 of photodetectors 205 in detector sub-module 500 according to a first embodiment. In this embodiment, the photodetectors 205 on the left side of row 600 are electrically coupled in parallel to each other, and the photodetectors 205 on the right side of row 600 are electrically coupled in parallel to each other. The photodetectors 205 on the left and right sides of row 600 are not electrically coupled to each other. Instead, the photodetectors 705 on the left and right sides of row 600 are electrically isolated from each other and from the photodetectors 205 in other rows. The left and right side of each row 600 is electrically coupled to a preamplifier, which can be or comprise any preamplifier known in the art, including charge-sensitive preamplifiers, transimpedance preamplifiers, and low-noise RF amplifiers.

A first side of the photodetectors 205 on the left side of row 600 is electrically connected to a first common cathode (e.g., cathode 1). A second side of the photodetectors 205 on the left side of row 600 is electrically connected to a first common anode (e.g., anode 1). A first side of the photodetectors 205 on the right side of row 600 is electrically connected to a second common cathode (e.g., cathode 2) that is different than the first common cathode. A second side of the photodetectors 205 on the right side of row 600 is electrically connected to a second common anode (e.g., anode 2) that is different than the first common anode.

The output of each side of row 600 is a differential signal 610. The differential signal 610 can substantially improve rejection of common-mode signals, which can occur when the left and right sides of row 600 are connected to a common cathode and/or anode, or if the left and right sides of row 600 are coupled to ground. In high-sensitivity circuits, common-mode noise can be picked up through electromagnetic interference, as well as through power supply coupling to the diode bias.

FIG. 7 is an alternative schematic circuit diagram 70 that is identical to schematic circuit diagram 60 except that in schematic circuit diagram 70 the load resistors $R_{load1L}$, $R_{load1R}$ have a resistance that is significantly lower than that of ground resistors 700 (e.g., significantly less than 10 kOhms), allowing the differential signal to primarily flow through $R_{load1L}$, $R_{load1R}$ due to resistive power splitting.

FIG. 8 is a schematic circuit diagram 80 of a representative row 800 of photodetectors 205 in detector sub-module 500 to form a differential signal output according to a second embodiment. In this embodiment, the photodetectors 205 on the left side of row 800 are electrically coupled in series to each other, and the photodetectors 205 on the right side of row 800 are electrically coupled in series to each other. The photodetectors 205 on the left and right sides of row 800 are not electrically coupled to each other. Instead, the photodetectors 205 on the left and right sides of row 800 are electrically isolated from each other and from the photodetectors 205 in other rows.

In schematic circuit diagram 80, a biasing connection (Vbias) is made through a 10 kOhm biasing resistor 810 on the left and right sides of row 800. In addition, the load resistors $R_{load1L}$, $R_{load1R}$ are split into two arms, one for each end of the differential readout and having half of the total load resistance, and are referenced to ground. Capacitive coupling through capacitors C are used to provide high-pass coupling of the pulsed response to the differential amplifiers. The high-frequency ground (RF ground) can be isolated from the bias ground to further suppress noise.

Figure 9:
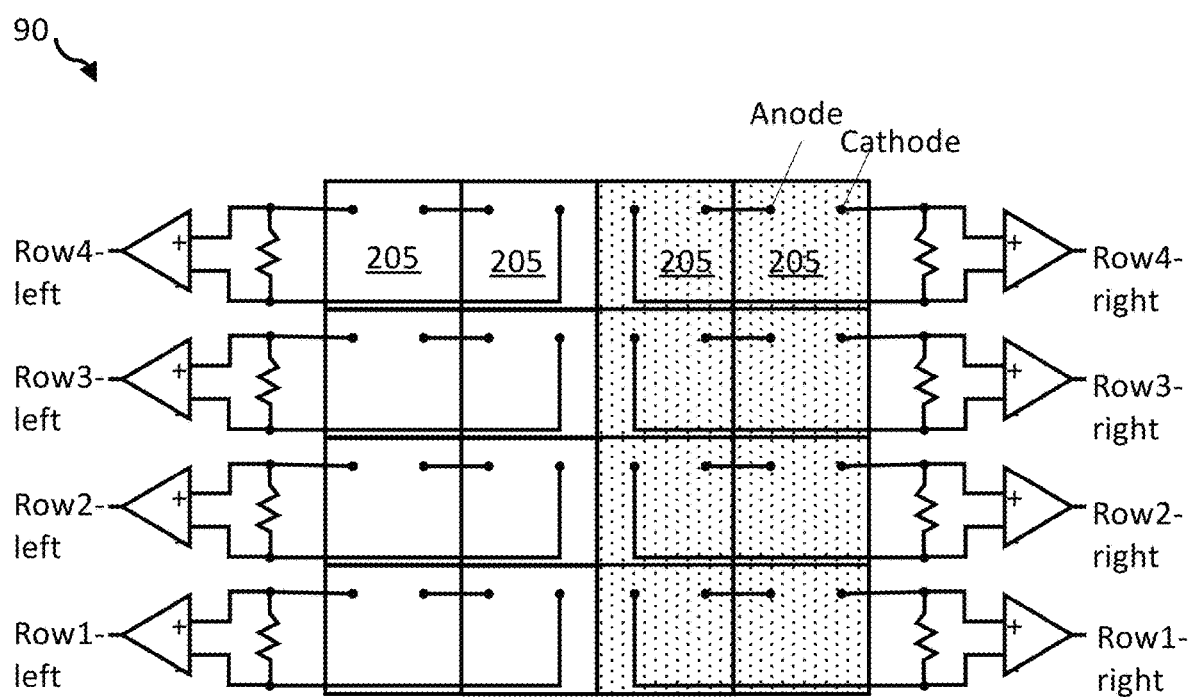
FIG. 9 is a schematic circuit diagram illustrating the split-row readout lines in the common PCB to form a differential signal output.

FIG. 9 is a schematic connection diagram 90 illustrating the split-row readout lines in the common PCB to form a differential signal output when using series-connected photodetector array elements. Schematic connection diagram 90 can be the same as schematic circuit diagrams 70 and/or 80.

In a split-row readout, the relative position of the light beam with respect to the X axis is related to and/or can be determined by the equation:

$$X_{position} = \frac{Row1_{left} - Row1_{right}}{Row1_{left} + Row1_{right}} \quad (1)$$

For example, when the X component of the beam is centered between the left and right sides of row 1, the magnitude of the $Row1_{left}$ output signal is equal to (or approximately equal to) the magnitude of the $Row1_{right}$ output signal and the $X_{position}$ is 0, which represents the middle of the row 1. When the beam is on the far-left side of row 1, the magnitude of the $Row1_{right}$ output signal approaches 0 and the $X_{position}$ approaches 1. When the beam is on the far-right side of row 1, the magnitude of the $Row1_{left}$ output signal approaches 0 and the $X_{position}$ approaches −1. In a preferred embodiment, the circuit diagram 60 should be constructed and configured so that the beam will be at least partially detected on each side of a row to improve detection accuracy of the beam, for example in the Y direction. In this embodiment, the $X_{position}$ can have a range of about −0.9 to +0.9.

It is noted that in ideal case, the relative magnitudes of $Row1_{left}$ and $Row1_{right}$ are linear with respect to the beam position (e.g., so that the $X_{position}$ is determined in a linear manner). However, in practice they have a non-linear relationship (e.g., a pincushion effect), typically with the leftmost and rightmost positions appearing to be closer to center than they are in reality.

In one embodiment, the row with the highest combined signal, amplitude, or power can be used to determine the "X" component or position of the beam. In another embodiment, the row with the highest combined signal or amplitude and the two nearest neighbor rows of that row can be used to can be used to determine the "X" component or position of the beam. Using additional rows, such as 3 or more rows, to determine the "X" component or position of the beam can improve the signal-to-noise ratio (SNR) in some embodiments.

In a split-row readout, the "Y" component or position of the light beam is related to and/or can be determined by outputs of the 2 highest-amplitude rows:

$$Y_{position} = \frac{Y' - Y''}{Y' + Y''} \quad (2)$$

where:

$$Y' = Row_{left}' + Row_{right}' \text{ and} \quad (3)$$

$$Y'' = Row_{left}'' + Row_{right}'' \quad (4)$$

$Row_{left}'$ and $Row_{right}'$ are the left and right output signals, respectively, of the row with the highest magnitude signal, and $Row_{left}''$ and $Row_{right}''$ are the left and right output signals, respectively, of the row with the second-highest magnitude signal. The magnitude of a row refers to the combined output signal of the left and right sides (e.g., $Magnitude_{Row1} = Row1_{left} + Row1_{right}$ for row 1). In an alternative embodiment, the rows with the highest combined power can be used to determine the "Y" component or position of the beam.

When the Y component of the beam is centered between Row' and Row", the magnitude of those rows is equal (i.e., Y'=Y") and the $Y_{position}$ is 0 (meaning centered between the rows). When the Y component of the beam is only on Row', the magnitude of Row" approaches 0 and the $Y_{position}$ approaches 1. When the Y component of the beam is only on Row", the magnitude of Row' approaches 0 and the $Y_{position}$ approaches −1. In a preferred embodiment, the circuit diagram 60, 70, 80, and/or 90 should be constructed and configured so that the beam will be at least partially detected in at least 2 rows to improve detection accuracy, for example in the DOI or Z direction. In this embodiment, the $Y_{position}$ can have a range of about −0.9 to +0.9.

The combined signal output, amplitude, or power from at least two rows is generally used to determine the "Y" component or position of the light beam. The combined signal output, amplitude, or power from additional rows can be used to improve accuracy and/or SNR. For example, when the beam is centered between rows (i.e., $Y_{position}=0$), the combined signal output from additional rows may be used to determine the Y" component or position of the light beam with greater accuracy.

In a split-row readout, the depth-of-interaction (DOI) of the gamma ray or "Z" component of the light beam is related to the "width" or variance (in general, "signal magnitude width") of the combined output signals (signal magnitude) across multiple rows (e.g., 3 or more rows in some embodiments). In an alternative embodiment, the DOI of the gamma ray or "Z" component of the light beam is related to the "width" or variance of the combined power across multiple rows (e.g., 3 or more rows in some embodiments).

In general, there is a direct relationship between the signal magnitude width and the DOI. For example, when the DOI is relatively shallow (e.g., the light beam is absorbed by the scintillator 220 proximal to its upper surface near the spacer 210), the signal magnitude width is relatively narrow. In contrast, when the DOI is relatively deep (e.g., the light beam is absorbed by the scintillator 220 proximal to its bottom surface), the signal magnitude width is relatively wide. The signal magnitude width can be determined by fitting the total signal magnitude of each row to a curve (e.g., a Gaussian distribution) to determine the apparent width of the curve. In a preferred embodiment, the signal magnitude of at least 3 rows is fit to the curve. In some embodiment, the signal magnitude of at least 5 rows is fit to the curve. The signal magnitude width can be fit to the curve using least squares or other fitting techniques.

As an example, row 3 may have the highest-magnitude signal, rows 2 and 4 may have the second-highest magnitude signals, and rows 1 and 5 have the lowest magnitude signals. Since the output signal is spread across 5 rows, the DOI of the beam in this example may be relatively deep in the scintillator 220 (e.g., away from photodetector layer 200). In another example, row 3 may have the highest-magnitude signal, rows 2 and 4 may have the second-highest magnitude signals, and rows 1 and 5 have zero or negligible output signals. Since the output signal is spread across 3 rows, the DOI of the beam in this example may be relatively shallow in the scintillator 220 (e.g., close to photodetector layer 200).

The signal magnitude includes both the direct line-of-sight signal where the scintillation photons travel in a straight line from the point of Gamma ray absorption to the photodetectors, and indirect photons where the photons first strike one (or more) of the sidewalls before being collected by the photodetectors. Therefore, in general, the signal magnitude is the sum of two signals: one narrower (higher amplitude, narrow spread) for the direct line-of-sight signal and one wider (lower amplitude spread across more photodetectors) for the indirect signal. The lateral spread of the of the scintillation photons is therefore a complex combination of direct photons as well as indirect photons. It may be desirable to adjust the reflectivity of the sidewalls to maximize DOI resolution, such as by coating the sidewalls (and bottom face of the scintillator opposite the face with the photodetector array) with a light-absorbing material or paint.

In some embodiments, a fitting algorithm or a machine learning algorithm can this sum of amplitudes/signals relationship. Further improvement in estimation of the DOI may be possible using the magnitudes of each side of each row instead of using the combined output signal of the left and right sides of each row.

The DOI accuracy is limited in part by the thickness of scintillator 220 (e.g., about 3 mm to about 10 mm). In general, thinner scintillators can have better DOI accuracy. The minimum or preferred number of rows to determine the X, Y, and Z/DOI components of the light beam can be determined empirically and/or by calibrating the detector.

Figure 10:
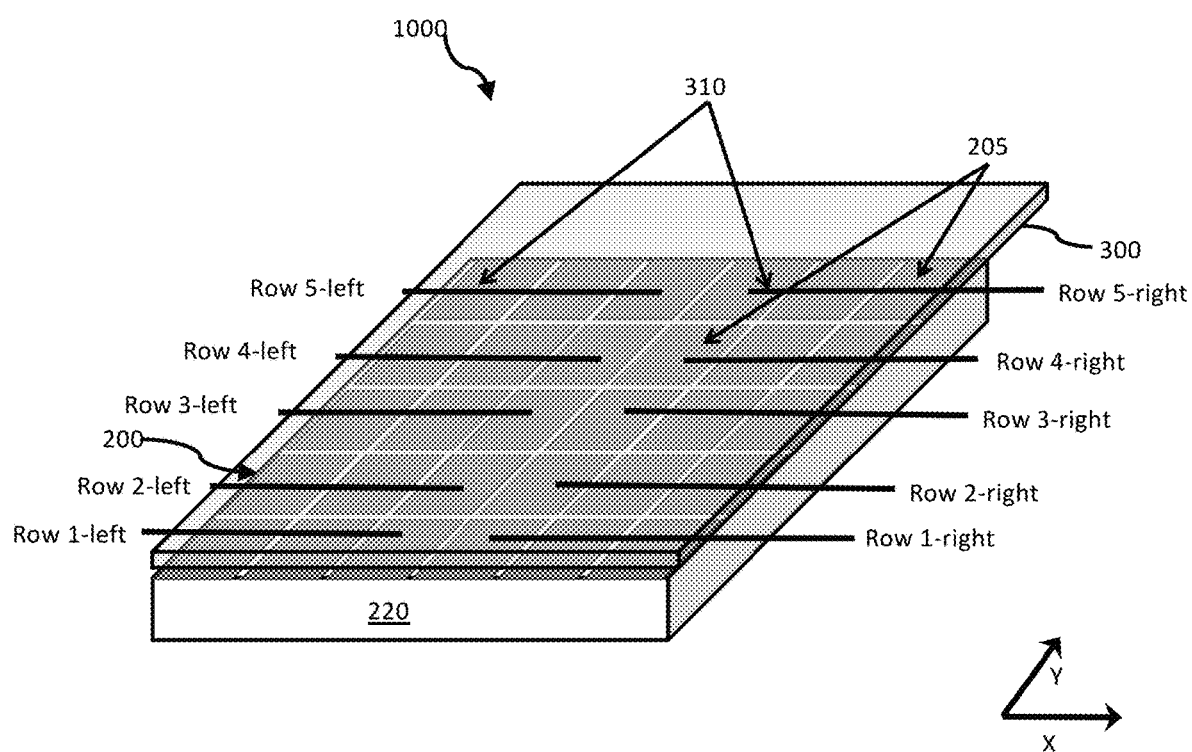
FIG. 10 is an alternative embodiment of the detector sub-module illustrated in FIG. 5.

The light-spreading layer 210 can help spread out the scintillator light/photons between rows and between left and right sides. In some embodiments, output signals from multiple rows and/or sides are used to determine the light beam position (X, Y, and Z/DOI). However, it may be possible to reduce the thickness of or eliminate the light-spreading layer 210 if reduced DOI accuracy is acceptable. An example of a sub-module 1000 for a thin-slab detector having a split-row readout of one-dimensional arrays of photodetector elements according to an alternative embodiment is illustrated in FIG. 10. Sub-module 1000 is identical to sub-module 500 except that sub-module 1000 does not include light-spreading layer 210.

Figure 11:
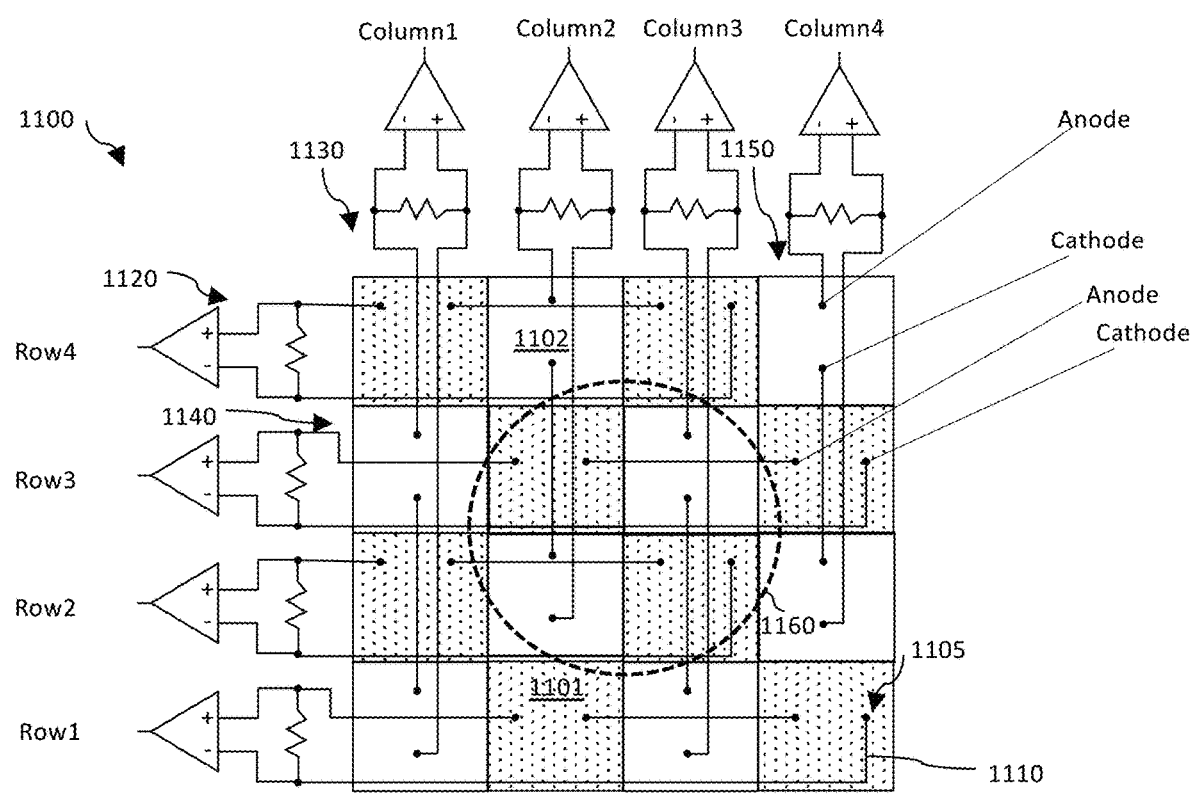
FIG. 11 is a schematic circuit diagram illustrating checkerboard readout lines in the common PCB.

FIG. 11 is a schematic connection diagram 1100 illustrating checkerboard readout lines in the common PCB according to an embodiment. The checkerboard readout lines are configured to electrically connect the photodetectors in a checkerboard grid pattern having an alternating arrangement of HA photodetectors 1101 and VA photodetectors 1102, which can be the same as photodetectors 205. The checkerboard grid includes horizontal arrays 1120 of HA photodetectors 1101 and vertical arrays 1130 of VA photodetectors 1102. The HA photodetectors 1101 are illustrated as patterned squares and the VA photodetectors 1102 are illustrated as white squares. The black dots 1105 represent the anode or cathode of each photodetector 1101, 1102 and the lines 1010 represent electrical connections. Additional details regarding the checkerboard configuration are disclosed in the '149 application.

In each horizontal array 1120, the HA photodetectors 1101 are electrically coupled in series to each other in a differential readout circuit. In each horizontal array 1120, the positive side of the differential readout circuit is electrically coupled to the anodes and cathodes of all HA photodetectors 1101 in the row and the negative side of the differential readout circuit is electrically coupled to only the cathode of one HA photodetector 1101 in the row, which functions as a common cathode connection. In an alternative embodiment, the negative side of the differential readout circuit is electrically coupled to only the anode of one HA photodetector 1101 in the row.

In each vertical array 1130, the VA photodetectors 1102 are electrically coupled in series to each other in a differential readout circuit. In each vertical array 1130, the positive side of the differential readout circuit is electrically coupled to the anodes and cathodes of all VA photodetectors 1102 in the column and the negative side of the differential readout circuit is electrically coupled to only the cathode of one VA photodetector 1102 in the column, which functions as a common cathode connection. In an alternative embodiment, the negative side of the differential readout circuit is electrically coupled to only the anode of one VA photodetector 1102 in the column.

The HA and VA photodetectors 1101, 1102 are arranged in rows 1140 and columns 150 to form the photodetector grid. Each row 1140 includes all of the HA photodetectors 1101 from a corresponding horizontal array 1120 and only one VA photodetector 1102 from each vertical array 1130 that falls within the respective row 1140. Similarly, each column 1150 includes all of the VA photodetectors 1102 from a corresponding vertical array 1130 and only one HA photodetector 1101 of each horizontal array 1120 that falls within the respective column 1150.

As can be seen, the photodetectors in each row 1140 have an alternating sequence of HA and VA photodetectors 1101, 1102 as illustrated by the alternating patterned and white squares. Likewise, the photodetectors in each column 1150 have an alternating sequence of HA and VA photodetectors 1101, 1102. In an embodiment, the alternating sequence of HA and VA photodetectors 1101, 1102 in each row 1140 and column 1150 form a checkerboard configuration.

The photodetector grid includes a rectangular (M×N) array or a square array of photodetectors, though other shapes are possible (e.g., circular arrays, oval arrays, triangular arrays, hexagonal arrays, or other shape arrays). In general, for an M×N array of photodetectors in a checkerboard configuration, where M and N are positive even integers, each row 1140 has M/2 HA photodetectors 1101 and each column 1150 has N/2 VA photodetectors 1102. When M equals N (in a square array), then each row 1140 has N/2 HA photodetectors 1101 and each column 1150 has N/2 VA photodetectors 1102. When M is a positive odd integer, the rows 1140 alternate between having (M+1)/2 HA photodetectors 1101 and (M−1)/2 HA photodetectors. Likewise, when N is a positive odd integer, the columns 1150 alternate between having (N+1)/2 VA photodetectors 1102 and (M−1)/2 VA photodetectors 1102.

The two-dimensional position of a light spot 1160 generated by an incident gamma ray can be determined by the ratio of the power output from each row 1140 (e.g., horizontal array 1120) and column 1150 (e.g., vertical array 1130). For example, if Power(Vertical_Array1+Vertical_Array2)/Power(Vertical_Array3+Vertical_Array4)=1, then the X position of light spot 1160 is centered, as it is in FIG. 11. Alternatively, the two-dimensional position of a light spot 1160 can be determined by the ratio of the maximum amplitude from each row 1140 (e.g., horizontal array 1120) and column 1150 (e.g., vertical array 1130).

A ratio less than 1 means that the X position of light spot 1160 is skewed towards columns 3 and 4. The ratio of Power(Vertical_Array3) and Power(Vertical_Array4) can be used to more precisely locate the center of the light spot 1160. For example, if this ratio is greater than 1, the light spot 1160 is skewed towards column 3. A ratio greater than 1 means that the X position of light spot 1160 is skewed towards columns 1 and 2. The ratio of Power(Vertical_Array1) and Power(Vertical_Array2) can be used to more precisely locate the center of the light spot 1160. The columns 1150 (e.g., vertical arrays 1130) having an output power above a threshold value can be determined before determining the X position of light spot 1160.

Similarly, if Power(Horizontal_Array1+Horizontal_Array2)/Power(Horizontal_Array3+Horizontal_Array4)=1, then the Y position of light spot 1160 is centered, as it is in FIG. 11. A ratio less than 1 means that the Y position of light spot 1160 is skewed towards rows 3 and 4. The ratio of Power(Horizontal_Array3) and Power(Horizontal_Array4) can be used to more precisely locate the center of the light spot 1160. A ratio greater than 1 means that the Y position of light spot 1160 is skewed towards rows 1 and 2. The ratio of Power(Horizontal_Array1) and Power(Horizontal_Array2) can be used to more precisely locate the center of the light spot 1160. The rows 1140 (e.g., horizontal arrays 1120) having an output power above a threshold value can be determined before determining the Y position of light spot 1160.

The Z position or DOI of the light spot 1160 can be determined by the variance of the power over the columns and rows. For example, in FIG. 11 only a small fraction of the light spot 1160 intersects row1, row4, column1, and column4. If the spot size were larger because the Z position or DOI of the gamma ray is further away from the array, then the power in row1, row4, column1, and column4 increases. Therefore, by individually reading out rows 1140 and columns 1150, the three-dimensional position (X, Y, and Z/DOI) of light spot 1160 can be determined simultaneously. In general, at least 3 rows 1140 and at least 3 columns 1150 are needed to determine the Z position or DOI.

The spot size of light spot 1160 can be determined based on the Z position or DOI (depth of interaction) of the gamma ray, as well as by the thickness of the light spreading layer. For example, thicker light spreading layers increase the lateral spread of the spot size. Conversely, thinner light spreading layers decrease the lateral spread of the spot size.

Figure 12:
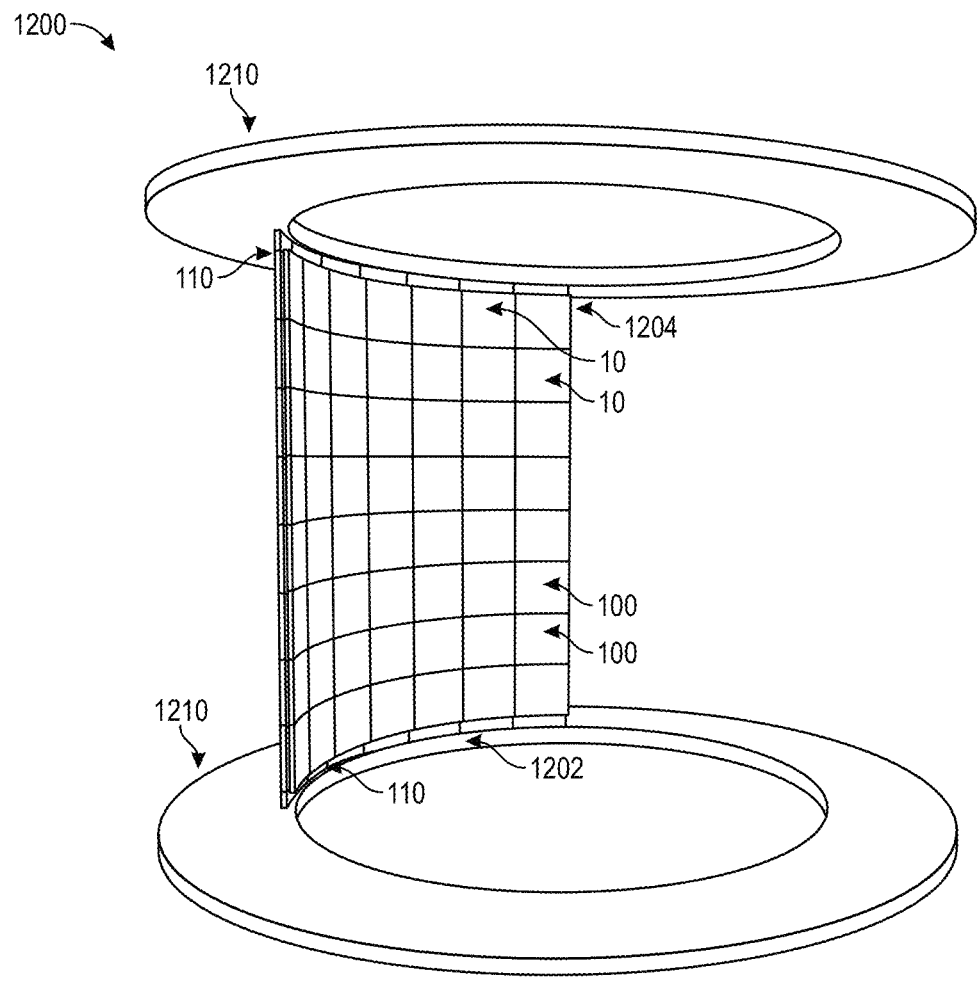
FIG. 12 is a schematic diagram of a portion of a cylindrical gamma ray detector according to an embodiment.

FIG. 12 is a schematic diagram of a portion of a cylindrical gamma ray detector 1200 according to an embodiment. The detector 1200 can be used as a PET camera. Detector 1200 includes a plurality of thin-slab detector modules 10 that are disposed adjacent to and parallel with each other to form a cylinder or annulus. The thin-slab detector modules 10 are mechanically supported by mechanical support rings 1210, which are attached to opposing first and second ends 1202, 1204 of the thin-slab detector modules 10. For example, the common PCB 110 can be used to mechanically connect the thin-slab detector modules 10 to the support rings 1210. The common PCB 110 can also be used to electrically couple the thin-slab detector modules 10 to the support rings 1210, for example as part of the read-out circuitry of the thin-slab detector modules 10.

The position in 3D space of each sub-module 100 can be encoded in the respective long-slab detector module 10 (i.e. element 1 through N) and in the sub-module's relative and/or absolute position on the support ring 1210. This makes it easy to use identical modules 10 and determine the precise position (e.g., X, Y, Z position), and the angle of each sub-module 100 and of each long-slab 60 based on the electrical readout of the detector 1200.

Technical advantages of the detector 1200 can include one or more of the following. First, the thin layers of each sub-module 100 can automatically confine the DOI to thickness Z1. Second, the thin layers of each sub-module 100 minimize sidewall reflections (e.g., scintillation light is isotropic—most goes up or down, only a small fraction laterally in thin slabs (e.g., between sub-modules 100), which can optimize light collection efficiency due to minimal sidewall reflection losses. Third, the X-Y localization of the light beam can be improved as a result of the thin Z thickness in each sub-module 100, which causes less lateral light spreading/blurring, improving X-Y resolution. Fourth, the thin Z thickness in each sub-module 100 can improve reduce the time between gamma ray absorption and scintillation light collection due to thin Z thickness, improving the timing performance of the detector 1200. Fifth, the detector 1220 can have reduced edge effects. The thin Z thickness in each sub-module 100 can reduce the effect of edge blurring in each sub-module 100, which typically has either a truncated round spot (absorbing sidewall) or a reflected spot that overlies the non-reflected spot (for reflecting sidewalls), shifting the apparent X-Y location.

Figure 13:
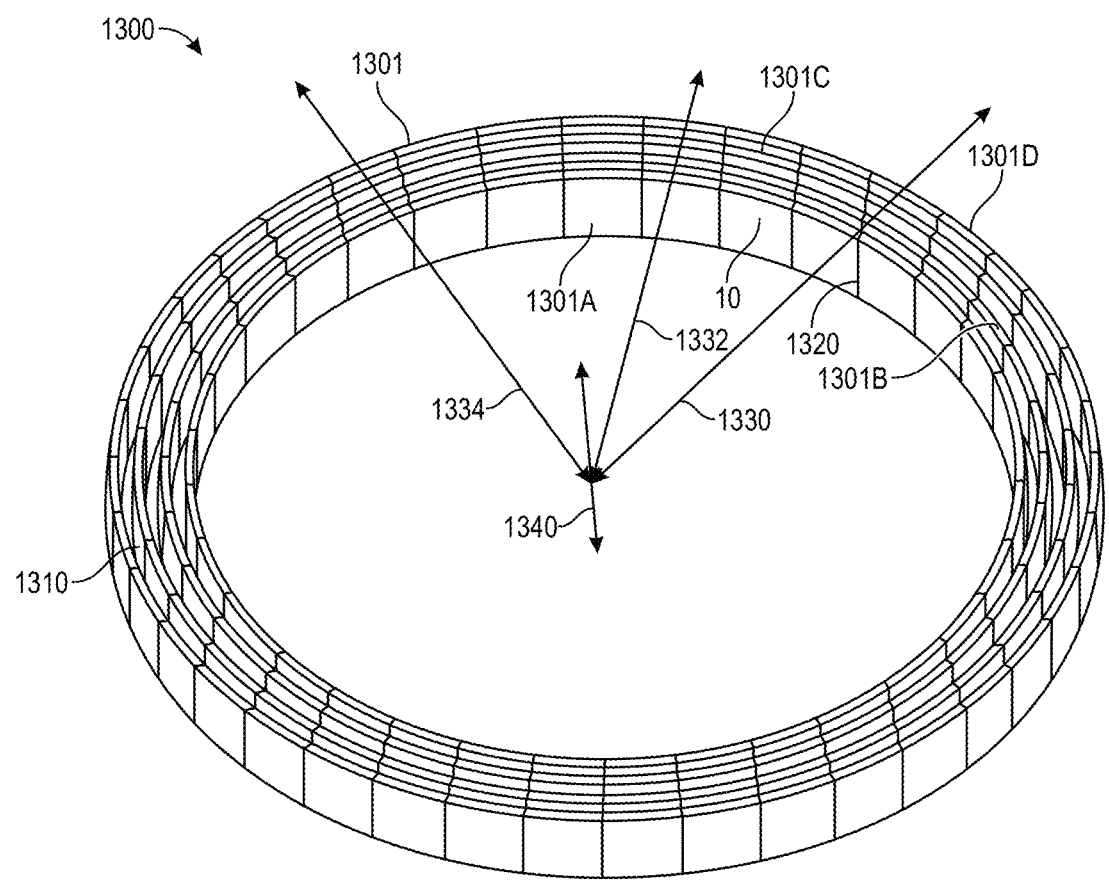
FIG. 13 is a schematic diagram of a portion of a cylindrical gamma ray detector according to another embodiment.

FIG. 13 is a schematic diagram of a portion of a cylindrical gamma ray detector 1300 according to another embodiment. The detector 1300 includes a plurality of concentric detection rings 1301. Though 4 detection rings 1301 are illustrated, there can be additional or fewer detection rings 1301 in other embodiments.

The detection rings 1301 can be mounted and/or electrically coupled to support rings such as support rings 1210. Each detection ring 1301 can have a respective support ring pair. Alternatively, two or more detection rings 1301 can share a common support ring pair.

The detection rings 1301 can be configured and arranged such that a thin air gap 1310 is formed between neighboring detection rings 1301. In one example, a first detection ring 1301A is formed of 25 thin-slab detector modules 10, a second detection ring 1301B is formed of 27 thin-slab detector modules 10, a third detection ring 1301C is formed of 29 thin-slab detector modules 10, a the fourth detection ring 1301D is formed of 31 thin-slab detector modules 10.

The detection rings 1310 can provide the ability to build up the required total thickness of scintillator (e.g., the effective scintillator thickness equal to the sum of the scintillator thickness in each ring 1301). Thus, the effective thickness of the scintillator can be customized as desired. This can increase gamma ray detection efficiency without sacrificing X, Y, Z, DOI, or energy resolution.

In addition, the thin layers (e.g., of each sub-module 100 in each thin-slab 10) enable Compton scatter tracking, particularly between different concentric detection rings 1301. As long as the first and second events are observed in different sub-modules 100 (inter-crystal scattering), excellent recovery can be achieved. In addition, timing can be used to determine the slab 10 or ring 1301 of first interaction.

Gamma ray energy can also be used to determine slab 10 or ring 1301 of first interaction in some circumstances. Whichever point (e.g., slab 10) has E<150 keV is the point of first interaction. If both points (e.g., slabs 10) have E>150 keV, then forward or backward scattering can occur. Since forward scattering is more likely to occur, the slab 10 closer to the gamma ray emission point is likely the slab 10 of first interaction. Though backward scattering can occur, it is often indistinguishable from forward scattering. Timing would be the best solution for determining which event occurred first. If the first and second events occur within the same slab 10 (intra-slab scattering), this is likely a near 90 degree scattering event where the energy deposited for both events is about the same. The net result will be a smearing of the apparent position, since the photodetector layer 200 outputs the weighted mean of the two positions. While such weighted-mean averaging occurs in nearly any gamma ray detector block configuration, the thin-slab configuration described herein has a relatively low intra-slab probability comparted to conventional designs. This means that the thin-slab configuration can more accurately recover the position of first interaction for most Compton scattering events, and for the small fraction of Compton scattering events that result in intra-slab conversion of both the first and second events, the blurring is no worse than for a conventional design.

An additional advantage of detector 1300 is that fabrication and assembly are straightforward. The detector 1300 can have a customized number and/or diameter of rings 1301. In addition the detector 1300 can be modularly built. In an embodiment, the rings 1301 can have a relatively large dimeter (e.g., about 65 cm or more) such as for whole body PET applications. In another embodiment, the rings 1301 can have a relatively medium dimeter (e.g., about 25 cm or more) such as for human brain PET applications. In another embodiment, the rings 1301 can have a relatively small diameter (e.g., less than 25 cm) such as for small animal PET applications. (e.g., rings 1401 having <25 cm diameter). Other diameters of rings 1301 and/or other applications of detector 1300 are possible.

The air gap 1310 between rings 1301 can have one or more advantages. For example, the air gap 1310 can enable cooling of rings 1301, slabs 10, detector modules 100, and/or readout electronics. For example, the air gap 1310 can provides physical space for any cooling hardware (e.g., air cooling, vapor cooling, and/or water cooling) and/or readout electronics. In addition, the air gaps 1310 increase the time difference between the first and second interaction for Compton events (provided both events do not happen within a single thin-slab layer 10). This time difference can be customized by adjusting the size of the air gaps 1310. In another example, the air gaps can eliminate and/or substantially reduce gap losses that occur between conventional rectangular block detectors arranged in a cylindrical geometry because inner diameter<outer diameter (trapezoidal blocks are needed to prevent these gaps). In the thin-slab design, each ring 1301 can have a different diameter to minimize these gaps. Fixed-sized slabs 10 can be used to increase ring diameter by adding additional slabs 10, which provides for modular manufacturability for reduced manufacturing costs and complexity.

An additional advantage of detector 1300 is to provide a more precise determination of the Compton scattering angle using the detector 1300 geometry and improved XYZ resolution of the thin slabs 10. Since the scattering angle is dependent on the energy deposited, this can be used to validate real events and reduce noise. The configuration of detector 1300 may allow the elimination of the need for detecting both ends of the LOR (i.e., single gamma ray detection instead of the coincidence detection of the two 511 keV gammas along the LOR.

The slabs 10 and rings 1301 can be positionally offset so that an inactive region in one ring can be covered by an active region in another ring. This can provide close to 100% coverage over the 360° rings 1301. For example, inner and/or outer ring(s) 1301 provide coverage for the inactive edge or gap 1320 between each slab 10 and for the inactive edge 120 (FIG. 1) between each sub-module 100 within a slab 10 that does not detect gamma rays. The inner and/or outer ring(s) 1401 also provide coverage for the inactive edge 230 (FIG. 2) between each photodetector 205 within a sub-module 100 which does not detect gamma rays.

For example, a first radial axis 1330 that passes through a first inactive edge or gap 1320 in ring 1301A can pass through an active slab 10 in ring 1301B. In another example, a second radial axis 1332 that passes through an inactive edge 120 between each sub-module 100 in ring 1301B can pass through an active sub-module 100 in ring 1301C. In yet another example, a third radial axis 1334 that passes through an inactive edge 230 between adjacent photodetectors 205 in ring 1301C can pass through an active photodetector 205 in ring 1301D. Each radial axis 1330, 1332, 1334 is orthogonal to a central axis 1340 that passes through the center of detector 1300 and/or the center of rings 1301.

Figure 14:
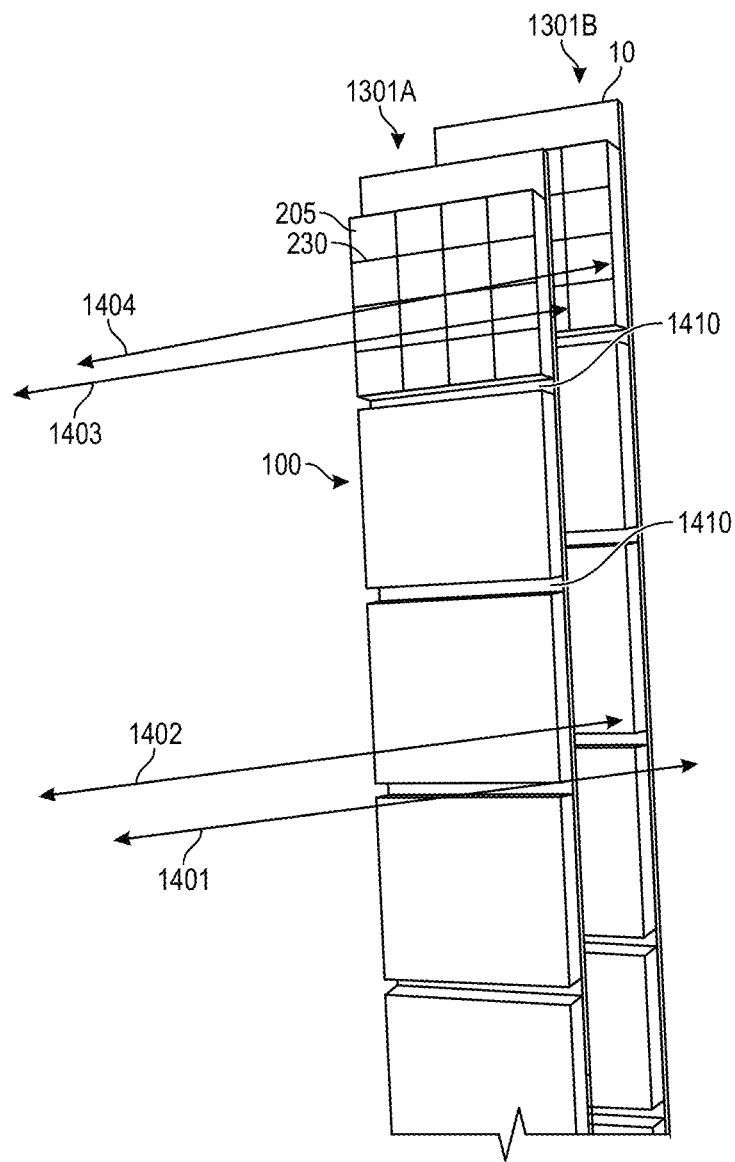
FIG. 14 is a detailed view of the overlap of representative first and second rings in detector illustrated in FIG. 13.

FIG. 14 is a detailed view of the overlap of representative first and second rings 1301A, 1301B in detector 1300. A first radial axis 1401 passes through a gap 1410 between adjacent detector sub-modules 100 in ring 1301A and passes through a detector sub-module 100 in ring 1301B. A second radial axis 1402 passes through a gap 1410 between adjacent detector sub-modules 100 in ring 1301B and passes through a detector sub-module 100 in ring 1301A. A third radial axis 1403 passes through an inactive edge 230 between adjacent photodetectors 205 in ring 1301A and passes through an active photodetector 205 in ring 1301B. A fourth radial axis 1404 passes through an inactive edge 230 between adjacent photodetectors 205 in ring 1301B and passes through an active photodetector 205 in ring 1301A. Each radial axis 1401-1404 is orthogonal to central axis 1340.

Figure 15:
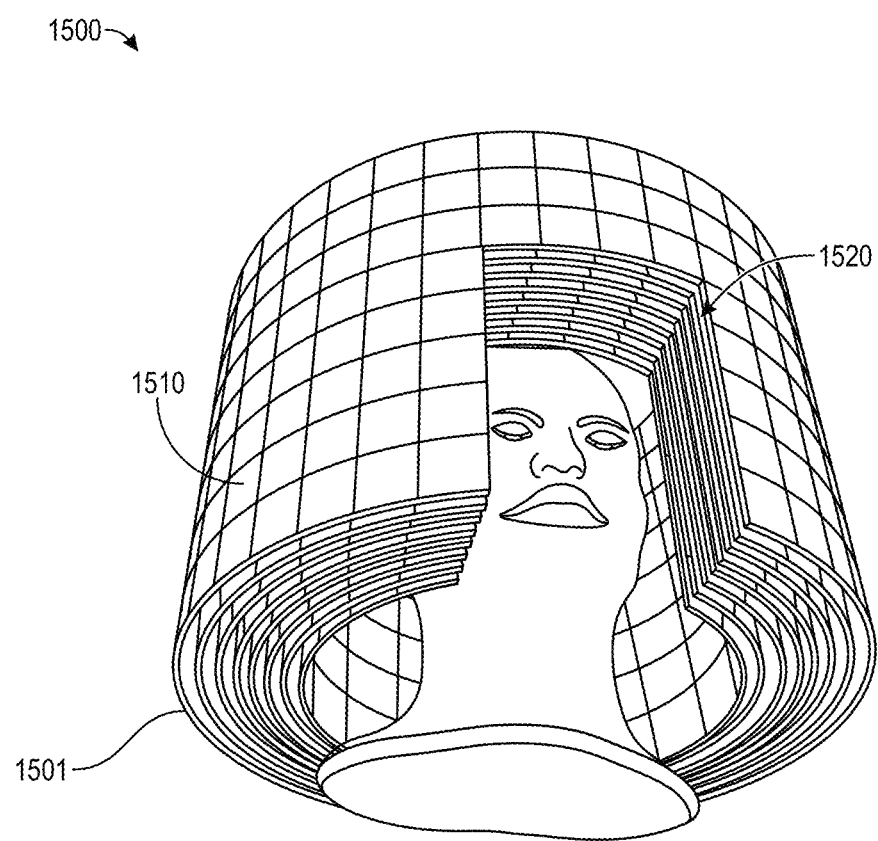
FIG. 15 is a perspective view of a PET camera that can be used for human brain scans according to an embodiment.

FIG. 15 is a perspective view of a PET camera 1500 that can be used for human brain scans according to an embodiment. The PET camera 1500 includes a plurality of (e.g., 8)

concentric layers 1501 of detectors. Each layer 1501 includes a plurality of (e.g., 8) rings 1510. Each ring 1510 can be the same as ring 1301. The rings 1510 in a first layer can have a different number of thin-slab detector modules 10 then the rings in a second layer, for example similar to the rings 1301 in FIG. 13. The PET camera 1500 has an optional opening 1520 which can be beneficial for patient comfort to reduce the feeling of claustrophobia by the camera 1500. The opening 1520 is formed by omitting thin-slab detector modules 10 in certain rings 1510 such that those rings include gaps or spaces that correspond to the opening 1520.

Figure 16:
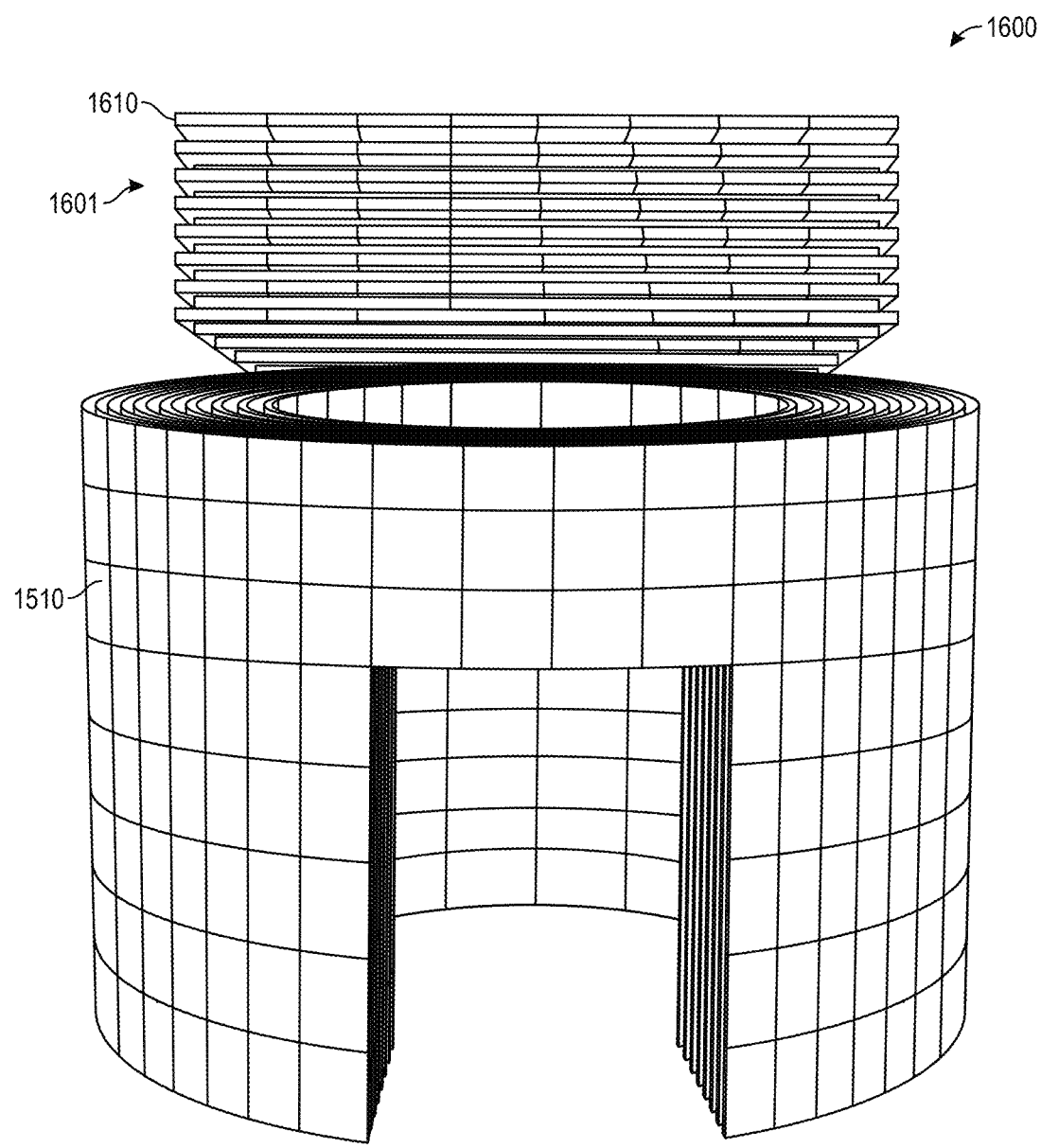
FIG. 16 is a side view of a PET camera according to an alternative embodiment.
Figure 17:
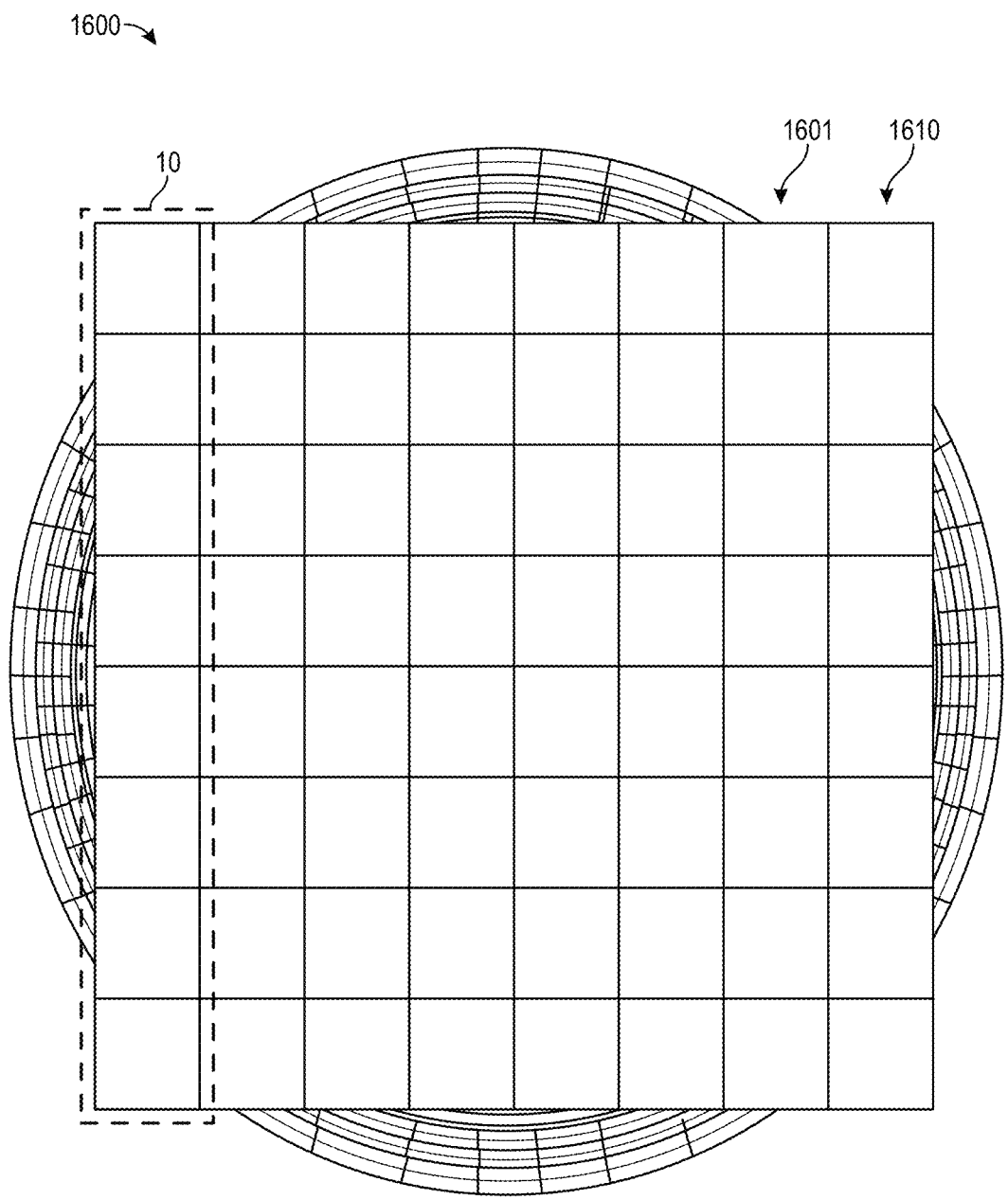
FIG. 17 is a top view of the PET camera illustrated in FIG. 16.

FIG. 16 is a side view of a PET camera 1600 according to an alternative embodiment. PET camera 1600 is the same as PET camera 1500 except that PET camera 1600 includes a "top hat" 1601. Top hat 1601 includes a plurality of stacked planar arrays 1610 of thin-slab detector modules 10. Each planar array 1610 includes a plurality of (e.g., 8) thin-slab detector modules 10. A top view of the PET camera 1600 is illustrated in FIG. 17, which further illustrates top hat 1601.

A technical advantage of the top-hat configuration includes that the top hat 1601 and cylindrical detector form a closed cylinder on one end to capture gamma rays that would otherwise be lost out the top of the head. The top hat 1601 can comprise an 8×1 array of long slabs 10 (or other array depending on the number n of long slabs 10) that forms an 8X×nY capture plane. Multiple 8×1 capture planes on top of each can be used to capture more gamma rays.

Figure 18:
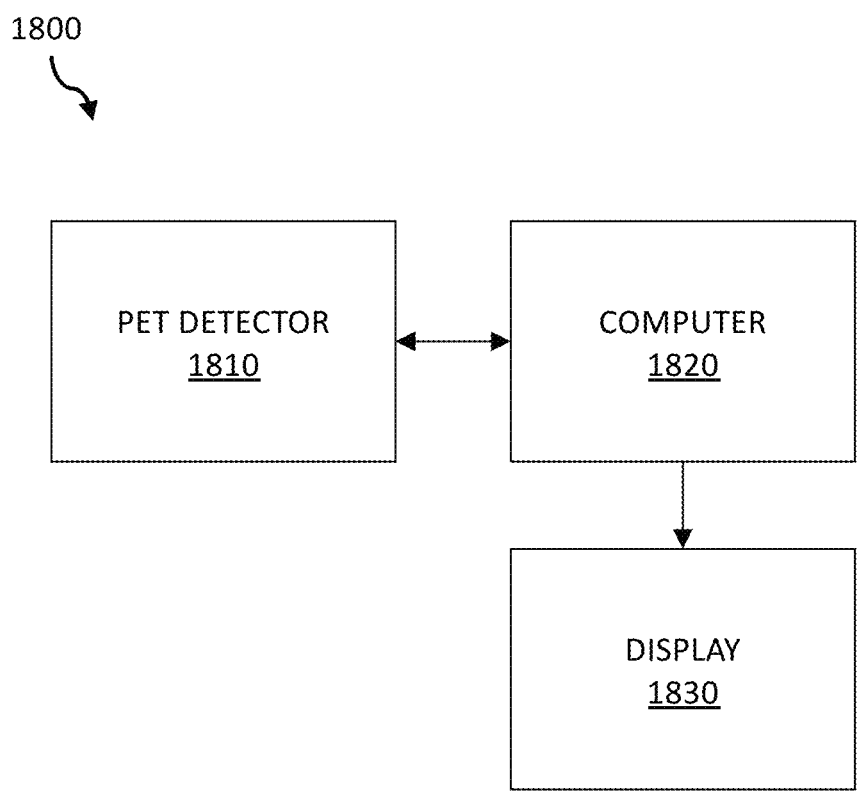
FIG. 18 is a block diagram of a PET detection system according to an embodiment.

FIG. 18 is a block diagram of a PET detection system 1800 according to an embodiment. System 1800 includes a PET detector 1810 and a computer 1820 that are electrically coupled together and/or in electrical communication with each other. The PET detector 1810 outputs electrical signals when gamma rays are incident on photodetectors in the PET detector 1810. The electrical signals are output through readout circuitry from PET detector 1810 to computer 1820. The computer 1820 includes a processor and non-volatile memory that stores computer-readable instructions that are executable by the processor. The computer-readable instructions are configured to determine the three-dimensional position (e.g., X, Y, and Z/DOI) of the incident gamma rays and associated light beam.

For example, the computer instructions can determine which ring 1301, which slab 10, and which detector sub-module 100 produced electrical signals in response to a detection event using detector 1300. The computer 1820 can include a look-up table or database that includes the relative or absolute coordinates of each ring 1301, slab 10, and sub-module 100 in detector 1300. The three-dimensional position within the sub-module 100 can be determined based on the configuration and readout circuitry of the photodetectors 205. For example, the X and Y positions can be determined in a first manner (e.g., according to Equations 1-4) when the photodetectors 205 are configured as one-dimensional split rows. The Z position or DOI can be determined by the fitting the total signal magnitude of each row to a curve, as discussed above. The X and Y positions can be determined a second manner (e.g., by the ratio of the power output from each row 1140 and column 1150) when the photodetectors 205 are configured in a checkerboard pattern. The Z position or DOI can be determined by the variance of the power over the columns and rows, as discussed above.

The computer 1820 can generate an output signal that represent the three-dimensional position of each incident gamma ray, which can be displayed on display 1830.

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure. The above-described embodiments may be implemented in numerous ways. One or more aspects and embodiments involving the performance of processes or methods may utilize program instructions executable by a device (e.g., a computer, a processor, or other device) to perform, or control performance of, the processes or methods.

In this respect, various inventive concepts may be embodied as a non-transitory computer readable storage medium (or multiple non-transitory computer readable storage media) (e.g., a computer memory of any suitable type including transitory or non-transitory digital storage units, circuit configurations in Field Programmable Gate Arrays or other semiconductor devices, or other tangible computer storage medium) encoded with one or more programs that, when executed on one or more computers or other processors, perform methods that implement one or more of the various embodiments described above. When implemented in software (e.g., as an app), the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more communication devices, which may be used to interconnect the computer to one or more other devices and/or systems, such as, for example, one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, a computer may have one or more input devices and/or one or more output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

The non-transitory computer readable medium or media may be transportable, such that the program or programs stored thereon may be loaded onto one or more different computers or other processors to implement various one or more of the aspects described above. In some embodiments, computer readable media may be non-transitory media.

The terms "program," "app," and "software" are used herein in a generic sense to refer to any type of computer code or set of computer-executable instructions that may be employed to program a computer or other processor to implement various aspects as described above. Additionally, it should be appreciated that, according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that performs particular tasks or implement particular abstract data types. The functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Thus, the present disclosure and claims include new and novel improvements to existing methods and technologies, which were not previously known nor implemented to achieve the useful results described above. Users of the present method and system will reap tangible benefits from the functions now made possible on account of the specific modifications described herein causing the effects in the system and its outputs to its users. It is expected that significantly improved operations can be achieved upon implementation of the claimed invention, using the technical components recited herein.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. A gamma-ray detector comprising:
   a plurality of modular one-dimensional arrays of monolithic detector sub-modules, each monolithic detector sub-module comprising:
      a scintillator layer;
      a light-spreading layer mounted on the scintillator layer; and
      a two-dimensional array of photodetectors that are arranged in columns and rows, the two-dimensional array of photodetectors mounted on the light-spreading layer; and
   a plurality of common printed circuit boards (PCBs), each common PCB electrically coupled to a respective modular one-dimensional array of monolithic detector sub-modules, each common PCB including, for each monolithic detector sub-module of the respective modular one-dimensional array of monolithic detector sub-modules:
      a corresponding first side output line electrically coupled to the two-dimensional array of photodetectors on a first side of each row; and
      a corresponding second side output line electrically coupled to the two-dimensional array of photodetectors on a second side of each row.

2. The gamma-ray detector of claim 1, wherein the light-spreading layer comprises a spacer layer.

3. The gamma-ray detector of claim 1, wherein in each monolithic detector sub-module:
   the two-dimensional array of photodetectors on the first side of each row are electrically coupled in series, and
   the two-dimensional array of photodetectors on the second side of each row are electrically coupled in series.

4. The gamma-ray detector of claim 3, wherein in each monolithic detector sub-module:
   the two-dimensional array of photodetectors on the first side of each row are configured to output a first differential signal, and
   the two-dimensional array of photodetectors on the second side of each row are configured to output a second differential signal.

5. The gamma-ray detector of claim 1, wherein in each monolithic detector sub-module:
   the two-dimensional array of photodetectors on the first side of each row are electrically coupled in parallel with each other, and
   the two-dimensional array of photodetectors on the second side of each row are electrically coupled in parallel with each other.

6. The gamma-ray detector of claim 5, wherein in each monolithic detector sub-module:
   the two-dimensional array of photodetectors on the first side of each row are configured to output a first differential signal, and
   the two-dimensional array of photodetectors on the second side of each row are configured to output a second differential signal.

7. The gamma-ray detector of claim 1, wherein a number of the two-dimensional array of photodetectors on the first side of each row is equal to a number of the two-dimensional array of photodetectors on the second side of each row.

8. The gamma-ray detector of claim 1, further comprising:
   a first support ring; and
   a second support ring,
   wherein:
      a first end of each common PCB is attached to the first support ring, and
      a second end of each common PCB is attached to the second support ring.

9. The gamma-ray detector of claim 8, wherein the first support ring includes electrical connections that are electrically coupled to each common PCB.

10. A gamma-ray detection system comprising:
    the gamma-ray detector of claim 1; and
    a computer in an electrical communication with the plurality of common PCBs, the computer configured to determine a first position of an incident gamma ray with respect to a first axis by determining:
       respective combined signal magnitudes of each row in the two-dimensional array of photodetectors, each respective combined signal magnitude equal to a respective sum of a respective first output magnitude of the first side of a respective row and a respective second output magnitude of the second side of the respective row, a highest-magnitude signal row having a highest combined signal magnitude of the respective combined signal magnitudes,
a relative first position of the incident gamma ray within the highest-magnitude signal row using the respective first output magnitude of the first side of the highest-magnitude signal row and the respective second output magnitude of the second side of the highest-magnitude signal row.

11. The gamma-ray detection system of claim 10, wherein the computer is further configured to determine:
a second-highest-magnitude signal row having a second-highest combined signal magnitude of the respective combined signal magnitudes, and
a relative second position of the incident gamma ray using the highest combined signal magnitude and the second-highest combined signal magnitude, the relative second position determined with respect to a second axis that is orthogonal to the first axis, wherein the second axis lies in a major plane defined by the two-dimensional array of photodetectors.

12. The gamma-ray detection system of claim 11, wherein the computer is further configured to determine:
a third-highest-magnitude signal row having a third-highest combined signal magnitude of the respective combined signal magnitudes, and
a relative third position of the incident gamma ray using the highest combined signal magnitude, the second-highest combined signal magnitude, and the third-highest combined signal magnitude, the relative third position determined with respect to a third axis that is orthogonal to the first axis and the second axis.

13. The gamma-ray detection system of claim 12, wherein the computer is further configured to determine:
the relative third position by fitting the highest combined signal magnitude, the second-highest combined signal magnitude, and the third-highest combined signal magnitude to a curve.

14. A gamma-ray detector comprising:
a plurality of modular one-dimensional arrays of monolithic detector sub-modules,
each monolithic detector sub-module comprising:
a scintillator layer;
a light-spreading layer mounted on the scintillator layer; and
a two-dimensional array of photodetectors that are arranged in columns and rows, the two-dimensional array of photodetectors mounted on the light-spreading layer, the two-dimensional array of photodetectors comprising:
horizontal arrays of HA photodetectors, HA photodetectors in each horizontal array electrically coupled in series to each other;
vertical arrays of VA photodetectors, VA photodetectors in each vertical array electrically coupled in series to each other,
wherein:
each row includes HA photodetectors from only one of the horizontal arrays of HA photodetectors and only one VA photodetector from each of a plurality of different vertical arrays of VA photodetectors,
each column includes VA photodetectors from only one of the vertical arrays of VA photodetectors and only one HA photodetector from each of a plurality of different horizontal arrays of HA photodetectors, and HA photodetectors and VA photodetectors are arranged in an alternating sequence to form a photodetector grid;
a plurality of common printed circuit boards (PCBs), each common PCB electrically coupled to a respective modular one-dimensional array of monolithic detector sub-modules, each common PCB including, for each monolithic detector sub-module of the respective modular one-dimensional array of monolithic detector sub-modules:
a plurality of HA output lines, each HA output line electrically coupled to the horizontal arrays of HA photodetectors in a respective monolithic detector sub-module, and
a plurality of VA output lines, each VA output line electrically coupled to the vertical arrays of VA photodetectors in the respective monolithic detector sub-module.

15. The gamma-ray detector of claim 14, wherein in each monolithic detector sub-module:
each HA output line is configured to output a first differential signal, and
each VA output line is configured to output a second differential signal.

16. The gamma-ray detector of claim 14, further comprising:
a first support ring; and
a second support ring,
wherein:
a first end of each common PCB is attached to the first support ring, and
a second end of each common PCB is attached to the second support ring.

17. The gamma-ray detector of claim 16, wherein the first support ring includes electrical connections that are electrically coupled to each common PCB.

18. A gamma-ray detection system comprising:
the gamma-ray detector of claim 14; and
a computer in an electrical communication with the plurality of common PCBs, the computer configured to determine a first position of an incident gamma ray with respect to a first axis by determining:
the vertical arrays of VA photodetectors having VA power outputs greater than a threshold power output, and
a relative first position of the incident gamma ray using the VA power outputs of the vertical arrays of VA photodetectors that are greater than the threshold power output.

19. The gamma-ray detection system of claim 18, wherein the computer is further configured to determine:
the horizontal arrays of HA photodetectors having HA power outputs greater than the threshold power output, and
a relative second position of the incident gamma ray using the HA power outputs of the horizontal arrays of HA photodetectors that are greater than the threshold power output, the relative second position determined with respect to a second axis that is orthogonal to the first axis, the first axis and the second axis parallel to the rows and the columns, respectively.

20. The gamma-ray detection system of claim 19, wherein the computer is further configured to determine a third position of the incident gamma ray using a variance of the HA power output and the VA power output that are greater than the threshold power output.

21. A gamma-ray detector comprising:
a plurality of modular one-dimensional arrays of monolithic detector sub-modules, each monolithic detector sub-module comprising:
a scintillator layer;
a light-spreading layer mounted on the scintillator layer; and
a two-dimensional array of photodetectors mounted on the light-spreading layer, the two-dimensional array of photodetectors arranged in columns and rows;
a plurality of common printed circuit boards (PCBs), each common PCB electrically coupled to a respective modular one-dimensional array of monolithic detector sub-modules; and
a first support ring and a second support ring,
wherein each common PCB includes, for each monolithic detector sub-module:
a corresponding first side output line electrically coupled to the two-dimensional array of photodetectors on a first side of each row, and
a corresponding second side output line electrically coupled to the two-dimensional array of photodetectors on a second side of each row,
wherein:
a first end of each common PCB is attached to the first support ring,
a second end of each common PCB is attached to the second support ring, and
the plurality of modular one-dimensional arrays of monolithic detector sub-modules forms an inner cylinder and an outer cylinder, the inner cylinder concentrically disposed within the outer cylinder.

22. The gamma-ray detector of claim 21, wherein the inner cylinder and the outer cylinder are spaced apart to form an air gap therebetween.

23. The gamma-ray detector of claim 21, wherein the plurality of modular one-dimensional arrays of monolithic detector sub-modules in the outer cylinder are positionally offset with respect to the plurality of modular one-dimensional arrays of monolithic detector sub-modules in the inner cylinder.

24. The gamma-ray detector of claim 23, wherein:
a central axis passes through a center of the inner cylinder and the outer cylinder,
a first radial axis passes through a first gap between adjacent monolithic detector sub-modules in a first inner modular one-dimensional array in the inner cylinder, the first radial axis orthogonal to the central axis, and
the first radial axis passes through a first outer monolithic detector sub-module in a first outer modular one-dimensional array in the outer cylinder.

25. The gamma-ray detector of claim 24, wherein:
a second radial axis passes through a second gap between adjacent monolithic detector sub-modules in a second outer modular one-dimensional array in the outer cylinder, the second radial axis orthogonal to the central axis, and
the second radial axis passes through a first inner monolithic detector sub-module in a second inner modular one-dimensional array in the inner cylinder.

26. The gamma-ray detector of claim 25, wherein:
a third radial axis passes through a first inactive edge between adjacent photodetectors in a second inner monolithic detector sub-module in a third inner modular one-dimensional array in the inner cylinder, the third radial axis orthogonal to the central axis, and
the third radial axis passes through an active photodetector in a second outer monolithic detector sub-module in a third outer modular one-dimensional array in the outer cylinder.

27. The gamma-ray detector of claim 26, wherein:
a fourth radial axis passes through a second inactive edge between adjacent photodetectors in a third outer monolithic detector sub-module in a fourth outer modular one-dimensional array in the outer cylinder, the fourth radial axis orthogonal to the central axis, and
the fourth radial axis passes through an active photodetector in a third inner monolithic detector sub-module in a fourth inner modular one-dimensional array in the inner cylinder.

* * * * *